US007623624B2

United States Patent
Moon et al.

(10) Patent No.: US 7,623,624 B2
(45) Date of Patent: Nov. 24, 2009

(54) METHOD AND APPARATUS FOR LABELING USING OPTICAL IDENTIFICATION ELEMENTS CHARACTERIZED BY X-RAY DIFFRACTION

(75) Inventors: John A. Moon, Wallingford, CT (US); Martin A. Putnam, Cheshire, CT (US); Alan D. Kersey, South Glastonbury, CT (US); Paul Szczepanek, Aptos, CA (US)

(73) Assignee: Illumina, Inc., San Diego, CA (US)

( * ) Notice: Subject to any disclaimer, the term of this patent is extended or adjusted under 35 U.S.C. 154(b) by 121 days.

(21) Appl. No.: 11/601,584

(22) Filed: Nov. 16, 2006

(65) Prior Publication Data

US 2007/0121181 A1    May 31, 2007

Related U.S. Application Data

(60) Provisional application No. 60/738,687, filed on Nov. 22, 2005.

(51) Int. Cl.
    *G01N 23/20* (2006.01)
(52) U.S. Cl. ........................................ 378/71
(58) Field of Classification Search ............... 378/70, 378/71, 75
    See application file for complete search history.

(56) References Cited

U.S. PATENT DOCUMENTS

| 3,614,193 | A |   | 10/1971 | Beiser |
| 3,858,979 | A | * | 1/1975  | Elbe ............................ 356/30 |
| 3,880,497 | A | * | 4/1975  | Bryngdahl .................. 359/238 |
| 3,891,302 | A |   | 6/1975  | Dabby |
| 3,903,415 | A | * | 9/1975  | Holzapfel .................... 378/75 |
| 3,916,182 | A |   | 10/1975 | Dabby |
| 3,968,476 | A |   | 7/1976  | McMahon |
| 4,011,435 | A |   | 3/1977  | Phelps |
| 4,023,010 | A |   | 5/1977  | Horst |
| 4,053,228 | A |   | 10/1977 | Schiller |
| 4,053,433 | A |   | 10/1977 | Lee |
| 4,131,337 | A |   | 12/1978 | Moraw |
| 4,168,146 | A |   | 9/1979  | Grubb |
| 4,301,139 | A |   | 11/1981 | Feingers |

(Continued)

FOREIGN PATENT DOCUMENTS

CH           598661           5/1978

(Continued)

OTHER PUBLICATIONS

Jain KK, Nanodiagnostics: Application of Nanotechnology in Molecular Diagnostics, Expert Review of Molecular Diagnostics 3(2):153-161 (2003), XP008038849.

(Continued)

*Primary Examiner*—Chih-Cheng G Kao
(74) *Attorney, Agent, or Firm*—Small Patent Law Group; Dean D. Small; Jason P. Gross

(57) ABSTRACT

An optical identification element for identifying an item. The optical identification element includes a binder material and one or more materials embedded in the binder material. The one or more materials provides an encoded composite X-ray diffraction pattern when illuminated by an X-ray beam. The encoded composite X-ray diffraction pattern is indicative of the item.

33 Claims, 18 Drawing Sheets

U.S. PATENT DOCUMENTS

| | | |
|---|---|---|
| 4,386,274 A | 5/1983 | Altshuler |
| 4,400,616 A | 8/1983 | Chevillat |
| 4,445,229 A | 4/1984 | Tasto |
| 4,447,546 A | 5/1984 | Hirschfeld |
| 4,537,504 A | 8/1985 | Baltes |
| 4,560,881 A | 12/1985 | Briggs |
| 4,562,157 A | 12/1985 | Lowe |
| 4,647,544 A | 3/1987 | Nicoli |
| 4,678,752 A | 7/1987 | Thorne |
| 4,685,480 A | 8/1987 | Eck |
| 4,688,240 A * | 8/1987 | Hosemann et al. ............ 378/70 |
| 4,690,907 A | 9/1987 | Hibino |
| 4,701,754 A | 10/1987 | Provonchee |
| 4,716,121 A | 12/1987 | Block |
| 4,725,110 A | 2/1988 | Glenn |
| 4,740,468 A | 4/1988 | Weng |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A * | 9/1988 | Carveth et al. .............. 206/219 |
| 4,807,950 A | 2/1989 | Glenn |
| 4,815,027 A | 3/1989 | Tokumitsu |
| 4,816,659 A | 3/1989 | Bianco |
| 4,822,746 A | 4/1989 | Walt |
| 4,841,140 A | 6/1989 | Sullivan |
| 4,877,747 A | 10/1989 | Stewart |
| 4,880,752 A | 11/1989 | Keck |
| 4,882,288 A | 11/1989 | North |
| 4,921,805 A | 5/1990 | Gebeyehu |
| 4,931,384 A | 6/1990 | Layton |
| 4,937,048 A | 6/1990 | Sakai |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason |
| RE33,581 E | 4/1991 | Nicoli |
| 5,028,545 A | 7/1991 | Soini |
| 5,030,558 A | 7/1991 | Litman |
| 5,033,826 A | 7/1991 | Kolner |
| 5,065,008 A | 11/1991 | Hakamata |
| 5,067,155 A | 11/1991 | Bianco |
| 5,081,012 A | 1/1992 | Flanagan |
| 5,089,387 A | 2/1992 | Tsay |
| 5,090,807 A | 2/1992 | Tai |
| 5,091,636 A | 2/1992 | Takada |
| 5,095,194 A | 3/1992 | Barbanell |
| 5,100,238 A | 3/1992 | Nailor |
| 5,104,209 A | 4/1992 | Hill |
| 5,105,305 A | 4/1992 | Betzig |
| 5,114,864 A | 5/1992 | Walt |
| 5,115,121 A | 5/1992 | Bianco |
| 5,118,608 A | 6/1992 | Layton |
| 5,129,974 A | 7/1992 | Aurenius |
| 5,138,468 A | 8/1992 | Barbanell |
| 5,141,848 A | 8/1992 | Donovan |
| 5,143,853 A | 9/1992 | Walt |
| 5,144,461 A | 9/1992 | Horan |
| 5,160,701 A | 11/1992 | Brown, III |
| 5,166,813 A | 11/1992 | Metz |
| 5,192,980 A | 3/1993 | Dixon |
| 5,196,350 A | 3/1993 | Backman |
| 5,200,794 A | 4/1993 | Nishiguma |
| 5,218,594 A | 6/1993 | Tanno |
| 5,239,178 A | 8/1993 | Derndinger |
| 5,244,636 A | 9/1993 | Walt |
| 5,283,777 A | 2/1994 | Tanno |
| 5,291,006 A | 3/1994 | Nishiguma |
| 5,291,027 A | 3/1994 | Kita |
| 5,300,764 A | 4/1994 | Hoshino |
| 5,307,332 A | 4/1994 | Tinet |
| 5,310,686 A | 5/1994 | Sawyers |
| 5,329,352 A | 7/1994 | Jacobsen |
| 5,342,790 A | 8/1994 | Levine |
| 5,349,442 A | 9/1994 | Deason |
| 5,352,582 A | 10/1994 | Lichtenwalter |
| 5,364,797 A | 11/1994 | Olson |
| 5,367,588 A | 11/1994 | Hill |
| 5,372,783 A | 12/1994 | Lackie |
| 5,374,816 A | 12/1994 | Bianco |
| 5,374,818 A | 12/1994 | Bianco |
| 5,388,173 A | 2/1995 | Glenn |
| 5,394,234 A | 2/1995 | Bianco |
| 5,395,558 A | 3/1995 | Tsai |
| 5,426,297 A | 6/1995 | Dunphy |
| 5,432,329 A | 7/1995 | Colgate |
| 5,442,433 A | 8/1995 | Hoshino |
| 5,448,659 A | 9/1995 | Tsutsui |
| 5,451,528 A | 9/1995 | Raymoure |
| 5,455,178 A | 10/1995 | Fattinger |
| 5,461,475 A | 10/1995 | Lerner |
| 5,465,176 A | 11/1995 | Bianco |
| 5,468,649 A | 11/1995 | Shah |
| 5,506,674 A | 4/1996 | Inoue |
| 5,514,785 A | 5/1996 | Van Ness |
| 5,528,045 A | 6/1996 | Hoffman |
| 5,547,849 A | 8/1996 | Baer |
| 5,559,613 A | 9/1996 | Deveaud-Pledran |
| 5,585,639 A | 12/1996 | Dorsel |
| 5,587,832 A | 12/1996 | Krause |
| 5,607,188 A | 3/1997 | Bahns |
| 5,610,287 A | 3/1997 | Nikiforov |
| 5,620,853 A | 4/1997 | Smethers |
| 5,621,515 A | 4/1997 | Hoshino |
| 5,624,850 A | 4/1997 | Kumar |
| 5,625,472 A | 4/1997 | Mizrahi |
| 5,627,040 A | 5/1997 | Bierre |
| 5,627,663 A | 5/1997 | Horan |
| 5,633,724 A | 5/1997 | King |
| 5,633,790 A | 5/1997 | Gritter |
| 5,633,975 A | 5/1997 | Gary |
| 5,663,790 A | 9/1997 | Ekstrom |
| 5,667,976 A | 9/1997 | Van Ness |
| 5,671,308 A | 9/1997 | Inoue |
| 5,682,244 A | 10/1997 | Barlow |
| 5,712,912 A | 1/1998 | Tomko |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins |
| 5,745,617 A | 4/1998 | Starodubov |
| 5,759,778 A | 6/1998 | Li |
| 5,760,961 A | 6/1998 | Tompkin |
| 5,766,956 A | 6/1998 | Groger |
| 5,771,251 A | 6/1998 | Kringlebotn |
| 5,776,694 A | 7/1998 | Sheiness |
| 5,793,502 A | 8/1998 | Bianco |
| 5,798,273 A | 8/1998 | Shuler |
| 5,799,231 A | 8/1998 | Gates |
| 5,801,857 A | 9/1998 | Heckenkamp |
| 5,804,384 A | 9/1998 | Muller |
| 5,812,272 A | 9/1998 | King |
| 5,822,472 A | 10/1998 | Danielzik |
| 5,824,478 A | 10/1998 | Muller |
| 5,824,557 A | 10/1998 | Burke et al. |
| 5,830,622 A | 11/1998 | Canning |
| 5,831,698 A | 11/1998 | Depp |
| 5,837,475 A | 11/1998 | Dorsel |
| 5,837,552 A | 11/1998 | Cotton |
| 5,841,555 A | 11/1998 | Bianco |
| 5,846,737 A | 12/1998 | Kang |
| 5,874,187 A | 2/1999 | Colvin |
| 5,881,197 A | 3/1999 | Dong |

| | | | | | | |
|---|---|---|---|---|---|---|
| 5,895,750 | A | 4/1999 | Mushahwar | 6,321,007 B1 | 11/2001 | Sanders |
| 5,922,550 | A | 7/1999 | Everhart | 6,322,932 B1 | 11/2001 | Covin |
| 5,922,617 | A | 7/1999 | Wang | RE37,473 E | 12/2001 | Challener |
| 5,925,562 | A | 7/1999 | Nova | 6,329,963 B1 | 12/2001 | Chiabrera |
| 5,925,878 | A | 7/1999 | Challener | 6,331,273 B1 | 12/2001 | Nova |
| 5,945,679 | A | 8/1999 | Dorsel | 6,340,588 B1 | 1/2002 | Nova |
| 5,972,542 | A | 10/1999 | Starodubov | 6,352,854 B1 | 3/2002 | Nova |
| 5,976,896 | A | 11/1999 | Kumar | 6,355,198 B1 | 3/2002 | Kim |
| 5,981,166 | A | 11/1999 | Mandecki | 6,355,432 B1 | 3/2002 | Fodor |
| 5,986,838 | A | 11/1999 | Thomas, III | 6,356,681 B1 | 3/2002 | Chen |
| 5,989,923 | A | 11/1999 | Lowe | 6,359,734 B1 | 3/2002 | Staub |
| 5,992,742 | A | 11/1999 | Jannson et al. | 6,361,958 B1 | 3/2002 | Shieh |
| 5,998,796 | A | 12/1999 | Liu | 6,363,097 B1 | 3/2002 | Linke |
| 6,001,510 | A | 12/1999 | Meng | 6,371,370 B2 | 4/2002 | Sadler |
| 6,005,691 | A | 12/1999 | Grot | 6,372,428 B1 | 4/2002 | Nova |
| 6,017,754 | A | 1/2000 | Chesnut | 6,383,754 B1 | 5/2002 | Kaufman |
| 6,025,129 | A | 2/2000 | Nova | 6,391,562 B2 | 5/2002 | Kambara |
| 6,025,283 | A | 2/2000 | Roberts | 6,395,558 B1 | 5/2002 | Duveneck |
| 6,027,694 | A | 2/2000 | Boulton | 6,399,295 B1 | 6/2002 | Kaylor |
| 6,030,581 | A | 2/2000 | Virtanen | 6,399,935 B1 | 6/2002 | Jovin |
| 6,035,082 | A | 3/2000 | Murphy | 6,403,320 B1 | 6/2002 | Read |
| 6,036,807 | A | 3/2000 | Brongers | 6,406,841 B1 | 6/2002 | Lee |
| 6,043,880 | A | 3/2000 | Andrews | 6,406,848 B1 | 6/2002 | Bridgham |
| 6,046,925 | A | 4/2000 | Tsien | 6,416,714 B1 | 7/2002 | Nova |
| 6,049,727 | A | 4/2000 | Crothall | 6,416,952 B1 | 7/2002 | Pirrung |
| 6,057,107 | A | 5/2000 | Fulton | 6,417,010 B1 | 7/2002 | Cargill |
| 6,060,256 | A | 5/2000 | Everhart | 6,428,707 B1 | 8/2002 | Berg et al. |
| 6,067,167 | A | 5/2000 | Atkinson | 6,428,957 B1 | 8/2002 | Delenstarr |
| 6,067,392 | A | 5/2000 | Wakami | 6,429,022 B1 | 8/2002 | Kunz |
| 6,078,048 | A | 6/2000 | Stevens | 6,433,849 B1 | 8/2002 | Lowe |
| 6,084,995 | A | 7/2000 | Clements | 6,436,651 B1 | 8/2002 | Everhart |
| 6,087,186 | A | 7/2000 | Cargill | 6,440,667 B1 | 8/2002 | Fodor |
| 6,096,496 | A | 8/2000 | Frankel | 6,456,762 B1 | 9/2002 | Nishiki |
| 6,096,596 | A | 8/2000 | Gonzalez | RE37,891 E | 10/2002 | Collins |
| 6,097,485 | A | 8/2000 | Lievan | 6,462,770 B1 | 10/2002 | Cline |
| 6,103,535 | A | 8/2000 | Pilevar | 6,489,606 B1 | 12/2002 | Kersey |
| 6,118,127 | A | 9/2000 | Liu | 6,496,287 B1 | 12/2002 | Seiberle |
| 6,128,077 | A | 10/2000 | Jovin | 6,506,342 B1 | 1/2003 | Frankel |
| 6,137,931 | A | 10/2000 | Ishikawa | 6,514,767 B1 | 2/2003 | Natan |
| 6,143,247 | A | 11/2000 | Sheppard, Jr. | 6,515,753 B2 | 2/2003 | Maher |
| 6,156,501 | A | 12/2000 | McGall | 6,522,406 B1 | 2/2003 | Rovira |
| 6,159,748 | A | 12/2000 | Hechinger | 6,524,793 B1 | 2/2003 | Chandler |
| 6,160,240 | A | 12/2000 | Momma | 6,533,183 B2 | 3/2003 | Aasmul |
| 6,160,656 | A | 12/2000 | Mossberg | 6,542,673 B1 | 4/2003 | Holter |
| 6,164,548 | A | 12/2000 | Curiel | 6,544,739 B1 | 4/2003 | Fodor |
| 6,165,592 | A | 12/2000 | Berger | 6,545,758 B1 | 4/2003 | Sandstrom |
| 6,165,648 | A | 12/2000 | Colvin et al. | 6,560,017 B1 | 5/2003 | Bianco |
| 6,174,648 | B1 | 1/2001 | Terao | 6,565,770 B1 | 5/2003 | Mayer |
| 6,194,563 | B1 | 2/2001 | Cruickshank | 6,576,424 B2 | 6/2003 | Fodor |
| 6,204,969 | B1 | 3/2001 | Jang | 6,578,712 B2 | 6/2003 | Lawandy |
| 6,214,560 | B1 | 4/2001 | Yguerabide | 6,592,036 B2 | 7/2003 | Sadler |
| 6,218,194 | B1 | 4/2001 | Lyndin | 6,594,421 B1 | 7/2003 | Johnson |
| 6,221,579 | B1 | 4/2001 | Everhart | 6,609,728 B1 | 8/2003 | Voerman et al. |
| 6,229,635 | B1 | 5/2001 | Wulf | 6,613,581 B1 | 9/2003 | Wada |
| 6,229,827 | B1 | 5/2001 | Fernald | 6,618,342 B1 | 9/2003 | Johnson |
| 6,229,941 | B1 | 5/2001 | Yoon | 6,622,916 B1 | 9/2003 | Bianco |
| 6,242,056 | B1 | 6/2001 | Spencer | 6,628,439 B2 | 9/2003 | Shiozawa |
| 6,259,450 | B1 | 7/2001 | Chiabrera | 6,632,655 B1 | 10/2003 | Mehta |
| 6,268,128 | B1 | 7/2001 | Collins | 6,635,470 B1 | 10/2003 | Vann |
| 6,277,628 | B1 | 8/2001 | Johann | 6,635,863 B1 | 10/2003 | Nihommori |
| 6,284,459 | B1 | 9/2001 | Nova | 6,646,243 B2 | 11/2003 | Pirrung |
| 6,285,806 | B1 | 9/2001 | Kersey | 6,657,758 B1 | 12/2003 | Garner |
| 6,288,220 | B1 | 9/2001 | Kambara | 6,660,147 B1 | 12/2003 | Woudenberg |
| 6,292,282 | B1 | 9/2001 | Mossberg | 6,678,429 B2 | 1/2004 | Mossberg |
| 6,292,319 | B1 | 9/2001 | Thomas, III | RE38,430 E | 2/2004 | Rosenstein |
| 6,301,047 | B1 | 10/2001 | Hoshino | 6,689,316 B1 | 2/2004 | Blyth |
| 6,304,263 | B1 | 10/2001 | Chiabrera | 6,692,031 B2 | 2/2004 | McGrew |
| 6,306,587 | B1 | 10/2001 | Royer | 6,692,912 B1 | 2/2004 | Boles |
| 6,309,601 | B1 | 10/2001 | Juncosa | 6,794,658 B2 | 9/2004 | MacAulay |
| 6,312,961 | B1 | 11/2001 | Voirin | 6,806,954 B2 | 10/2004 | Sandstrom |
| 6,313,771 | B1 | 11/2001 | Munroe | 6,858,184 B2 | 2/2005 | Pelrine |
| 6,314,220 | B1 | 11/2001 | Mossberg | 6,874,639 B2 | 4/2005 | Lawandy |
| 6,319,668 | B1 | 11/2001 | Nova | 6,881,789 B2 | 4/2005 | Bossé |

| | | |
|---|---|---|
| 6,892,001 B2 | 5/2005 | Ohta |
| 6,905,885 B2 | 6/2005 | Colston |
| 6,908,737 B2 | 6/2005 | Ravkin |
| 6,919,009 B2 | 7/2005 | Stonas et al. |
| 6,982,996 B1 | 1/2006 | Putnam |
| 7,045,049 B1 | 5/2006 | Natan et al. |
| 7,065,032 B2 | 6/2006 | Horimai |
| 7,092,160 B2 | 8/2006 | Putnam |
| 7,106,513 B2 | 9/2006 | Moon |
| 7,126,755 B2 | 10/2006 | Moon |
| 7,215,628 B2 | 5/2007 | Horimai |
| 7,225,082 B1 | 5/2007 | Natan |
| 7,321,541 B2 | 1/2008 | Horimai |
| 7,339,148 B2 | 3/2008 | Kawano |
| 7,349,158 B2 | 3/2008 | Moon |
| 2001/0007775 A1 | 7/2001 | Seul |
| 2002/0000471 A1 | 1/2002 | Aasmul |
| 2002/0006664 A1 | 1/2002 | Sabatini |
| 2002/0018430 A1 | 2/2002 | Heckenkamp |
| 2002/0021003 A1 | 2/2002 | McGrew |
| 2002/0022273 A1 | 2/2002 | Empedocles |
| 2002/0025534 A1 | 2/2002 | Goh |
| 2002/0031783 A1 | 3/2002 | Empedocles |
| 2002/0034747 A1 | 3/2002 | Bruchez |
| 2002/0039732 A1 | 4/2002 | Bruchez |
| 2002/0074513 A1 | 6/2002 | Abel |
| 2002/0084329 A1 | 7/2002 | Kaye |
| 2002/0090650 A1 | 7/2002 | Empedocles |
| 2002/0094528 A1 | 7/2002 | Salafsky |
| 2002/0097658 A1 | 7/2002 | Worthington |
| 2002/0155490 A1 | 10/2002 | Skinner |
| 2002/0174918 A1 * | 11/2002 | Fujimura et al. ............ 148/508 |
| 2002/0197456 A1 | 12/2002 | Pope |
| 2003/0008323 A1 | 1/2003 | Ravkin |
| 2003/0021003 A1 | 1/2003 | Ono |
| 2003/0032203 A1 | 2/2003 | Sabatini |
| 2003/0077038 A1 | 4/2003 | Murashima |
| 2003/0082568 A1 | 5/2003 | Phan |
| 2003/0082587 A1 | 5/2003 | Seul |
| 2003/0129654 A1 | 7/2003 | Ravkin |
| 2003/0138208 A1 | 7/2003 | Pawlak |
| 2003/0142713 A1 | 7/2003 | Lawandy |
| 2003/0153006 A1 | 8/2003 | Washizu |
| 2003/0162296 A1 | 8/2003 | Lawandy |
| 2003/0184730 A1 | 10/2003 | Price |
| 2003/0203390 A1 | 10/2003 | Kaye |
| 2003/0228610 A1 | 12/2003 | Seul |
| 2004/0027968 A1 | 2/2004 | Horimai |
| 2004/0047030 A1 | 3/2004 | MacAulay |
| 2004/0062178 A1 | 4/2004 | Horimai |
| 2004/0075907 A1 * | 4/2004 | Moon et al. .................. 359/566 |
| 2004/0100636 A1 | 5/2004 | Somekh |
| 2004/0100892 A1 | 5/2004 | Horimai |
| 2004/0125370 A1 | 7/2004 | Montagu |
| 2004/0125424 A1 | 7/2004 | Moon |
| 2004/0126875 A1 | 7/2004 | Putnam |
| 2004/0132205 A1 | 7/2004 | Moon |
| 2004/0156471 A1 * | 8/2004 | Sakata ........................ 378/35 |
| 2004/0170356 A1 | 9/2004 | Iazikov |
| 2004/0175842 A1 | 9/2004 | Roitman |
| 2004/0209376 A1 | 10/2004 | Natan |
| 2004/0233485 A1 | 11/2004 | Moon |
| 2004/0263923 A1 | 12/2004 | Moon |
| 2005/0042764 A1 | 2/2005 | Sailor |
| 2005/0220408 A1 | 10/2005 | Putnam |
| 2005/0227252 A1 | 10/2005 | Moon |
| 2005/0270603 A1 | 12/2005 | Putnam |
| 2006/0023310 A1 | 2/2006 | Putnam |
| 2006/0028727 A1 | 2/2006 | Moon |
| 2006/0050544 A1 | 3/2006 | Horimai |
| 2006/0057729 A1 | 3/2006 | Moon |
| 2006/0063271 A1 | 3/2006 | Putnam |
| 2006/0067179 A1 | 3/2006 | Matsumoto |
| 2006/0071075 A1 | 4/2006 | Moon et al. |
| 2006/0072177 A1 | 4/2006 | Putnam |
| 2006/0118630 A1 | 6/2006 | Kersey |
| 2006/0119913 A1 | 6/2006 | Moon |
| 2006/0132877 A1 | 6/2006 | Kersey |
| 2006/0134324 A1 | 6/2006 | Putnam |
| 2006/0139635 A1 | 6/2006 | Kersey |
| 2006/0140074 A1 | 6/2006 | Horimai |
| 2006/0160208 A1 | 7/2006 | Putnam |
| 2007/0121181 A1 | 5/2007 | Moon |
| 2008/0170664 A1 * | 7/2008 | Kalman ...................... 378/71 |
| 2008/0192311 A1 | 8/2008 | Horimai |
| 2009/0040885 A1 | 2/2009 | Horimai |

FOREIGN PATENT DOCUMENTS

| | | |
|---|---|---|
| DE | 2416652 | 10/1975 |
| EP | 0 395 300 | 10/1990 |
| EP | 0 723 149 | 7/1996 |
| EP | 0 798 573 A1 | 10/1997 |
| EP | 0 911 667 A1 | 4/1999 |
| EP | 916981 | 5/1999 |
| EP | 0 972 817 A1 | 1/2000 |
| EP | 1182054 | 2/2002 |
| EP | 1219979 | 7/2002 |
| GB | 2 118 189 | 10/1983 |
| GB | 2129551 | 5/1984 |
| GB | 2 138 821 | 10/1984 |
| GB | 2 299 235 | 9/1996 |
| GB | 2 306 484 | 5/1997 |
| GB | 2 319 838 | 6/1998 |
| GB | 2372100 | 8/2002 |
| JP | 58143254 A * | 8/1983 |
| JP | 08102544 | 4/1986 |
| JP | 01047950 | 2/1989 |
| JP | 10160705 | 6/1998 |
| JP | 11119029 | 4/1999 |
| JP | 2000-035521 | 2/2000 |
| JP | 00249706 | 9/2000 |
| JP | 200300467 A | 1/2003 |
| JP | 2003004671 A * | 1/2003 |
| WO | WO 91/06496 | 5/1991 |
| WO | WO 93/09668 | 5/1993 |
| WO | WO 94/28119 | 12/1994 |
| WO | WO 96/24061 | 8/1996 |
| WO | WO 96/36436 | 11/1996 |
| WO | WO 97/12680 | 4/1997 |
| WO | WO 97/15690 | 5/1997 |
| WO | WO 97/17258 | 5/1997 |
| WO | WO 97/31282 | 8/1997 |
| WO | WO 97/34171 | 9/1997 |
| WO | WO 98/04740 | 2/1998 |
| WO | WO 98/24549 | 6/1998 |
| WO | WO 99/02266 | 1/1999 |
| WO | WO 99/09042 | 2/1999 |
| WO | WO 99/32654 | 7/1999 |
| WO | WO 99/42209 | 8/1999 |
| WO | WO 00/08443 | 2/2000 |
| WO | WO0016893 | 3/2000 |
| WO | WO 00/37914 | 6/2000 |
| WO | WO 00/37969 | 6/2000 |
| WO | WO 00/39617 | 7/2000 |
| WO | WO0061198 | 10/2000 |
| WO | WO0158583 | 8/2001 |
| WO | WO0171322 | 9/2001 |
| WO | WO 01/78889 | 10/2001 |
| WO | WO0178889 | 10/2001 |
| WO | WO 02/596603 | 8/2002 |
| WO | WO02059306 | 8/2002 |
| WO | WO03061983 | 7/2003 |
| WO | WO03091731 | 11/2003 |
| WO | WO2004011940 | 2/2004 |
| WO | WO2004015418 | 2/2004 |

| | | |
|---|---|---|
| WO | WO 2004/025561 | 3/2004 |
| WO | WO 2004/025563 | 3/2004 |
| WO | WO2004019276 | 3/2004 |
| WO | WO2004024328 | 3/2004 |
| WO | WO2004025562 | 3/2004 |
| WO | WO2004046697 | 6/2004 |
| WO | WO 2005/026729 | 3/2005 |
| WO | WO 2005/027031 | 3/2005 |
| WO | WO 2005/029047 | 3/2005 |
| WO | WO 2005/033681 | 4/2005 |
| WO | WO 2005/050207 | 6/2005 |
| WO | WO 2005/079544 | 9/2005 |
| WO | WO 2006/020363 | 2/2006 |
| WO | WO 2006/055735 | 5/2006 |
| WO | WO 2006/055736 | 5/2006 |
| WO | WO 2006/076053 | 7/2006 |

OTHER PUBLICATIONS

Lide (CRC Handbook of Chemistry and Physics, 71st ed.), 1990, p. 6-8.

Othonos, X. Lee; Superimposed Multiple Bragg Gratings, Nov. 10, 1994, vol. 30, No. 23, Electronics Letters.

Patil et al. (AAPS PharmSciTech, Mar. 24, 2006, vol. 7, pp. E1-E7), Porous Polystyrene Beads for Self-Emulsifying System Containing Loratadine.

Po Ki Yuen, Microbarcode Sorting Device; Science & Technology, Corning Incorparated, Corning, New York 14831-0007, USA, Jul. 10, 2003.

International Search Report and Written Opinion for International Application No. PCT/US2003/26315, dated 2004.

International Search Report and Written Opinion for International Application No. PCT/US2003/26316, dated 2004.

International Search Report for International Application No. PCT/US2003/28862, dated Jan. 30, 2004.

International Search Report for International Application No. PCT/US2003/28874, dated Feb. 5, 2004.

International Search Report for International Application No. PCT/US2003/28875, dated Jan. 27, 2004.

International Search Report for International Application No. PCT/US2003/28887, dated Jan. 29, 2004.

International Search Report for International Application No. PCT/US2003/28890, dated Dec. 18, 2003.

International Search Report and Written Opinion for International Application No. PCT/US2003/29164, dated 2004.

International Search Report for International Application No. PCT/US2003/29244, dated Jan. 21, 2004.

International Search Report and Written Opinion for International Application No. PCT/US2004/30037, dated 2005.

International Search Report and Written Opinion for International Application No. PCT/US2004/30038, dated 2005.

International Search Report and Written Opinion for International Application No. PCT/US2004/30300, dated 2005.

International Search Report and Written Opinion for International Application No. PCT/US2004/32084, dated 2005.

International Search Report and Written Opinion for International Application No. PCT/US2004/38416, dated 2005.

International Search Report and Written Opinion for International Application No. PCT/US2005/05743, dated 2005.

"Compact Disc Arrayer"; V&P Scientific; Nov. 17, 2003; pp. 1-4.

"Electronically Scanned Confocal Imaging System"; IBM Technical Disclosure Bulletin; vol. 36; No. 06B; Jun. 1993; pp. 261-262.

"Ben Beune Patent Licensing Director of Philips IP&S"; Replication & Duplication—News & Technology; Jan.-Feb. 2002; pp. 1-2.

Andrew Marshall; "DNA Chips: Array of Possibilities"; Nature Biotechnology vol. 16 Jan. 1998; pp. 27-31.

de Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.

Fonjallaz et al., "Interferometric Side Diffraction Technique for the Characterisation of Fiber Gratings"; 1999 OSA Conference, Sep. 23-25; 3 pgs.

Hideki Kambara; Recent Progress In fluorescent DNA Analyzers and Methods; Current Topics in Analytical checmistry; vol. 1, (1998) pp. 21-36.

Ivan Oransky; "Sequencing on Compact Disc? Microgenomics of Breast Cancer; Better Binding Site Prediction"; vol. 17 / Issue 13 / 35 / Jun. 30, 2003; 13 pgs.

Kogelnik H; "Coupled Wave Theory for Thick Hologram Gratings"; The Bell System Technical Journal, 48(9):2909-2947 (1969).

Krug P., "Measurement of Index Modulation Along an Optical Fiber Bragg Grating"; Optics Letters, 20(17):1767-1769.

Leith et al., "Holographic Data Storage in Three-Dimensional Media"; Applied Optics, vol. 5, No. 8, Aug. 1966; 21 pgs.

Mark O. Worthington; "Curriculum Vitae"; Jan. 5, 2004; 4 pgs.

Masato Mitsuhashi; "Gene Manipulation on Plastic Plates"; Nature, vol. 357, Jun. 11, 1992; pp. 519-520.

Michael C. Needels et al.; "Generation and Screening of an Oligonucleotide-Encoded Synthetic Peptide Library"; Proc Natl. Acad. Sci. USA, vol. 90; pp. 10700-10704, Nov. 1993.

Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.

Shelia R. Nicerwarner-Peña, "Submicrometer Metallic Barcodes"; Science, vol. 294; Oct. 5, 2001; 5 pgs.

Thomas Laurell; "Enhanced Enzyme Activity in Silicon Integrated Enzyme Reactors Utilizing Porous Silicon as the Coupling Matrix"; Sensor & Actuators B 31(1996); pp. 161-166.

Vander Lugt; "Design Relationships for Holographic Memories"; Applied Optics, vol. 12, No. 7, Jul. 1973; pp. 1675-1685.

W.R. Rigby; "An Anodizing Process for the Production of Inorganic Microfiltration Membranes"; 2436Transactions of the Institute of Metal Finishing;68 Aug. (1990),Part 3 p. 95-98.

Yoshinobu Kohara; "DNA Probes on Beads Arrayed in a Capillary, 'Bead-Array',Exhibited High Hybridization Performance"; Nucleic Acids Research, 2002, vol. 30, No. 16 e87; 7 pgs.

"Introduction to Flow Cytometry: A Learning Guide," BD Biosciences, San Jose, CA, Apr. 2000.

US 6,780,301, 08/2004, Natan (withdrawn)

* cited by examiner

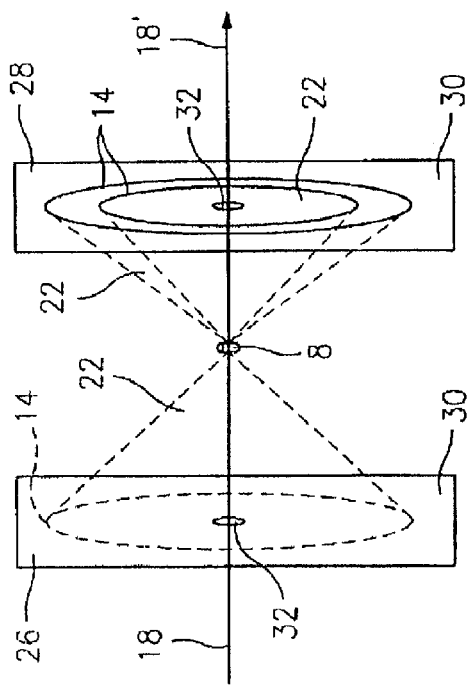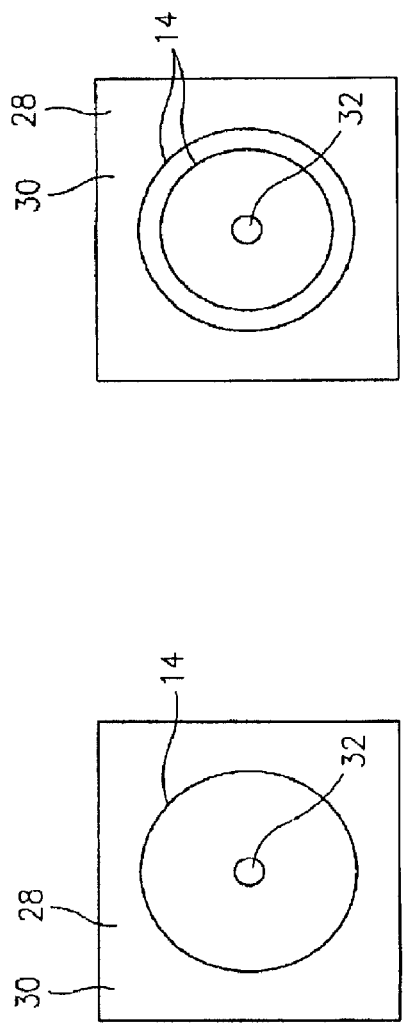
FIG. 2(a)
FIG. 2(b)
FIG. 2(c)

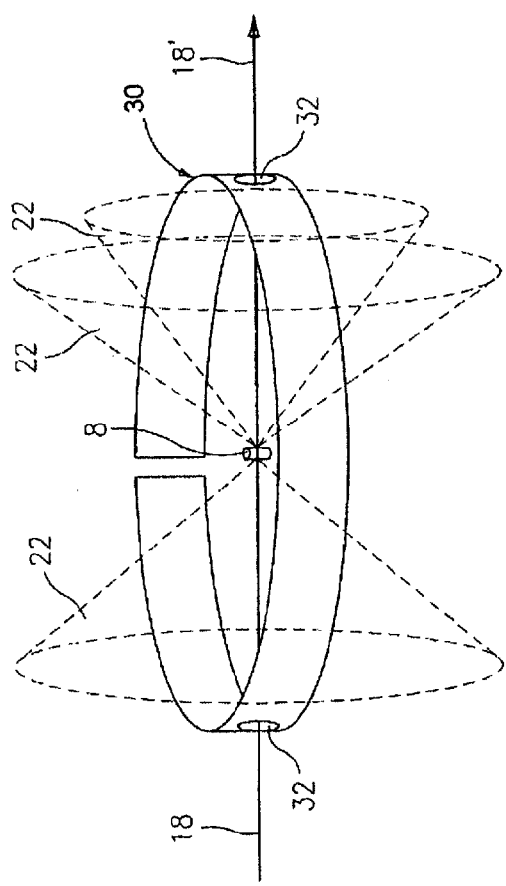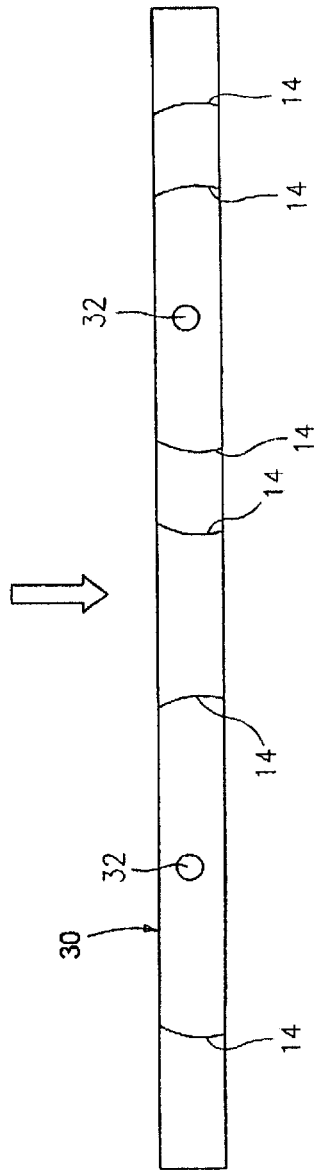
FIG. 3(a)
FIG. 3(b)

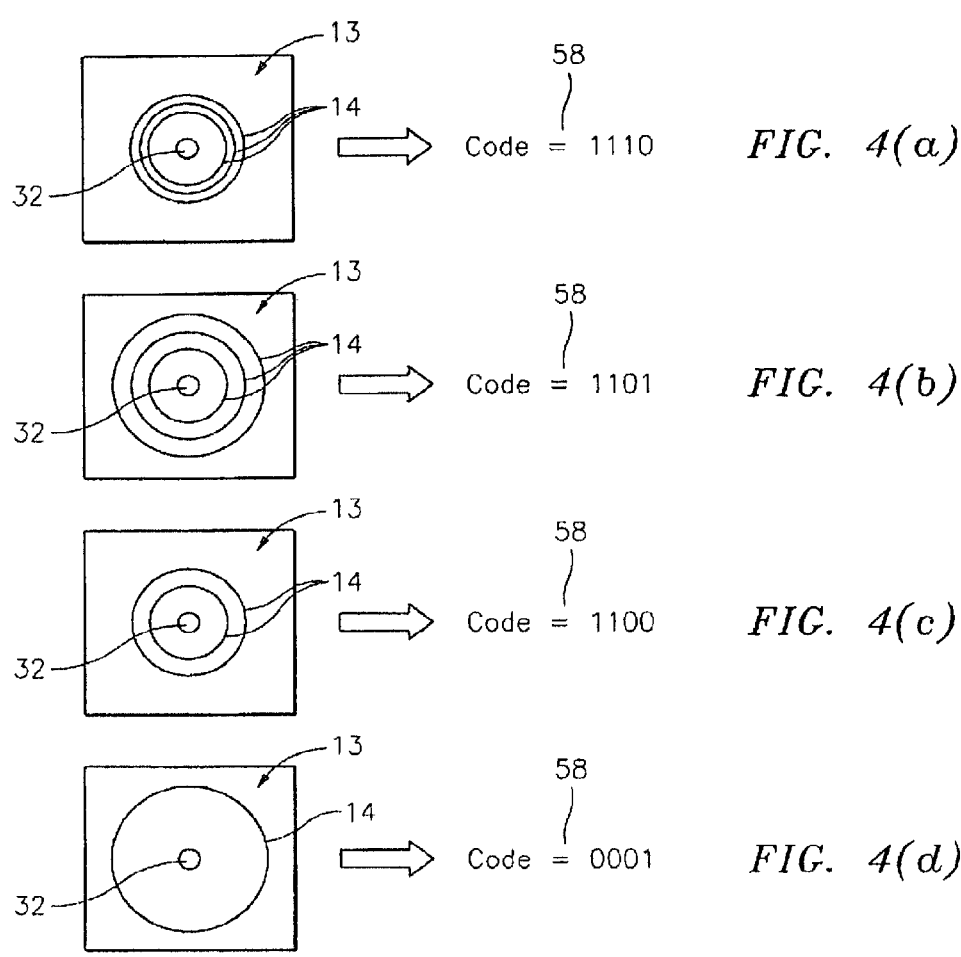

US 7,623,624 B2

METHOD AND APPARATUS FOR LABELING USING OPTICAL IDENTIFICATION ELEMENTS CHARACTERIZED BY X-RAY DIFFRACTION

CROSS REFERENCE TO RELATED APPLICATIONS

This application claims the benefit of U.S. Provisional Application No. 60/738,687, filed Nov. 22, 2005.

TECHNICAL FIELD

This invention relates to optical identification, and more particularly to a method and apparatus for labeling using optical identification elements characterized by X-ray diffraction.

BACKGROUND ART

It is often desirable to uniquely label or identify items, such as large or small objects, plants, and/or animals for sorting, tracking, identification, verification, authentication, or for other purposes. For example, in a form of chemical synthesis in combinatorial chemistry known as "solid phase" chemical synthesis, encoded beads or particles are used as a solid support for the synthesis of chemicals and or chemical libraries. The encoded beads or particles are used identify the attached chemicals.

In another example, in a DNA/genomic sequencing assay commonly referred to as a "random bead assay", known DNA sequences (probes) are attached to encoded beads or particles. The beads are then mixed with a labeled target analyte, and segments of the DNA sequence of the labeled target analyte will selectively bind to complementary DNA segments of the probe. The known probes are then spatially separated and examined for fluorescence. The beads that fluoresce indicate that the DNA sequence strands of the target analyte have attached or hybridized to the complementary DNA on that bead. The DNA sequences in the target analyte can then be determined by identifying the code on the bead, which uniquely identifies the complementary DNA (or cDNA) sequence of each probe. In addition the level of fluorescence is indicative of how many of the target molecules hybridized to the probe molecules for a given bead.

Existing technologies for uniquely labeling or identifying items, such as bar codes, electronic microchips/transponders, radio-frequency identification (RFID), and fluorescence (or other optical techniques), are often inadequate. For example, existing technologies may be too large for certain applications, may not provide enough different codes, may require specific alignment of particles to the detector, or cannot withstand harsh environments, e.g., harsh temperature, pressure, chemical, nuclear and/or electromagnetic environments.

Therefore, it would be desirable to obtain a labeling technique that provides the capability of providing many codes (e.g., greater than 1 million codes), that can be made very small, that can withstand harsh environments, and/or be independent of orientation with respect to the detector.

SUMMARY OF THE INVENTION

Objects of the present invention include provision of a labeling technique that allows for a large number of distinct codes, can be made very small, code is readable independent of orientation, and/or can withstand harsh environments.

According to a first aspect of the present invention, an optical identification element for identifying an item comprises a binder material and one or more materials embedded in the binder material. The one or more materials provide an encoded composite X-ray diffraction pattern when illuminated by an X-ray beam. The encoded composite X-ray diffraction pattern is indicative of the item.

According to a second aspect of the present invention, a method of labeling an item comprises: selecting at least one material from a plurality of materials having differing X-ray diffraction patterns; embedding the at least one material in a binder material to form at least one optical identification element; and physically associating the at least one optical identification element with the item. The at least one material provides an encoded composite X-ray diffraction pattern when illuminated by an X-ray beam, with the encoded composite X-ray diffraction pattern being indicative of the item.

According to a third aspect of the present invention, a method of identifying an item comprises: illuminating an optical identification element physically associated with the item using an X-ray beam; detecting a composite X-ray diffraction pattern from the illuminated optical identification element; and decoding the composite X-ray diffraction pattern to identify the item. In various embodiments, the decoding includes identifying at least a portion of Debye-Scherrer diffraction patterns in the composite X-ray diffraction pattern.

In various embodiments of the above aspects of the present invention, the encoded composite X-ray diffraction pattern is indicative of a binary or higher order. The number of bits in the binary code may correspond to the number of unique Debye-Scherrer diffraction patterns in the encoded composite X-ray diffraction pattern. The binary code may be arranged in a protocol including one or more error-check bits and a plurality of data bits.

In various embodiments of the above aspects of the present invention, the one or more materials is selected from powdered crystal materials. The binder material may be selected from glass, plastic, one or more polymers, and combinations including one or more of the foregoing.

In various embodiments of the above aspects of the present invention, the optical identification element is shaped as a microbead or a macrobead. Alternatively, the binder material may be in the form of a thread or fiber.

In various embodiments of the above aspects of the present invention, the item is selected from the group, comprising: large or small objects, products, solids, powders, liquids, gases, plants, currency, ID cards, minerals, cells and/or animals. The item may be a chemical or a DNA sequence.

The foregoing and other objects, features and advantages of the present invention will become more apparent in light of the following detailed description of exemplary embodiments thereof.

BRIEF DESCRIPTION OF THE DRAWINGS

FIG. 2 depicts front and back Debye-Scherrer diffraction patterns for an optical element including powdered crystals in accordance with various embodiments of the present invention.

FIG. 3 depicts a Debye-Scherrer camera.

FIG. 4 depicts encoded X-ray diffraction patterns in accordance with various embodiments of the present invention.

BEST MODE FOR CARRYING OUT THE INVENTION

Figure 1:
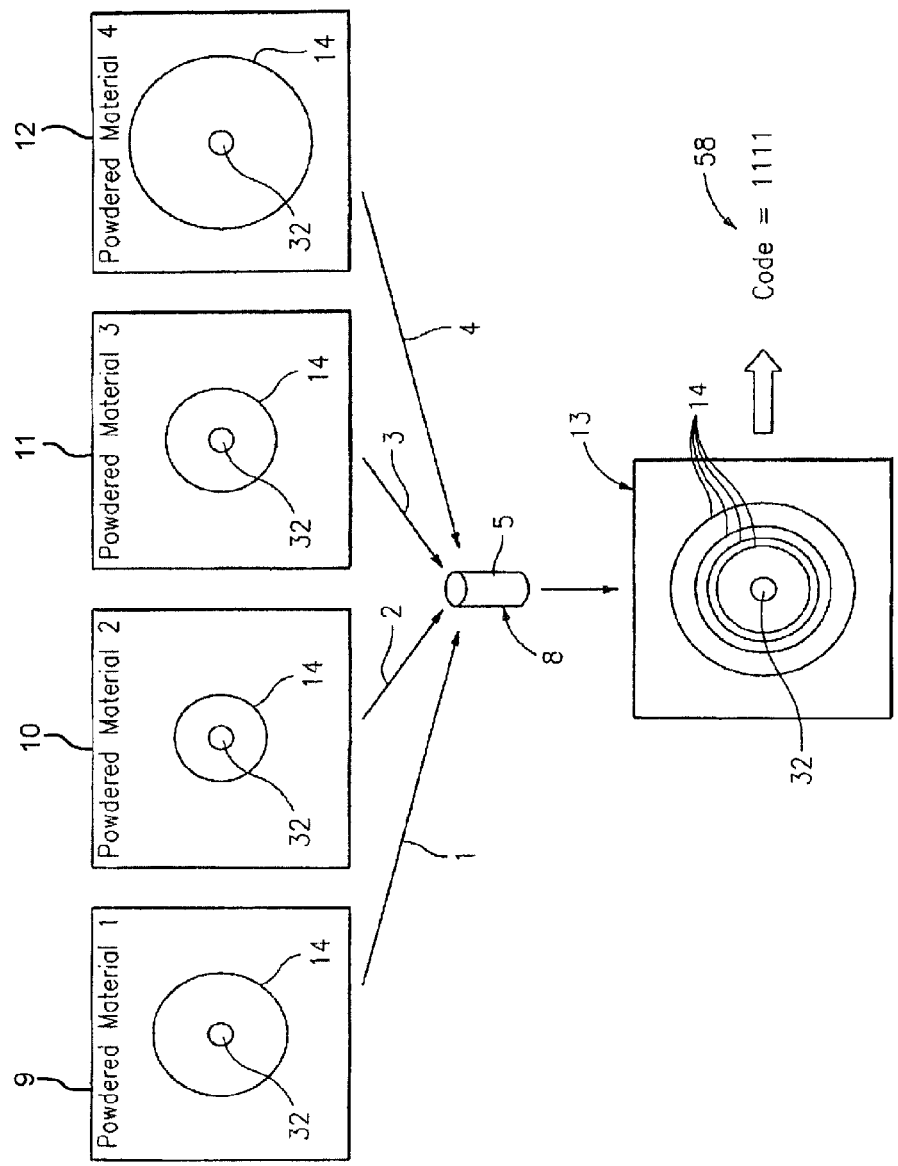
FIG. 1 is a schematic diagram illustrating a method for encoding an optical identification element in accordance with various embodiments of the present invention.

Referring to FIG. 1, an encoded optical identification element (element) 8 for identifying an item is shown. The optical identification element 8 is a composite structure formed from one or more materials 1-4 embedded in a binder material 5. In the example shown in FIG. 1, the optical identification element 8 is in the shape of a bead, and four different materials 1-4 are embedded in the binder material 5 to form the bead. As will be described in further detail hereinafter, any number of materials may be used, and the optical identification element 8 may take any convenient shape.

Each of the materials 1-4 provides a unique X-ray diffraction pattern, as indicated at 9-12 respectively, when illuminated by an X-ray beam. In the embodiment shown, the X-ray diffraction patterns 9-12 are rings 14, each of which are portions of a Debye-Scherrer diffraction pattern.

When the materials 1-4 are embedded in the binder material 5 to form the optical identification element 8, the X-ray diffraction patterns 9-12 of the materials 1-4 produce a composite X-ray diffraction pattern 13 for the optical identification element 8. In the present invention, the composite X-ray diffraction pattern 13 is encoded by the selection and omission of one or more of the different materials 1-4. A code 58 provided by the composite X-ray diffraction pattern 13 is used to identify an item physically associated with the optical identification element 8. By physically associated, it is meant that the optical identification element 8 is attached to, embedded in, disposed proximate to, mixed with, or otherwise located in some relationship to the item.

Preferably, each of the materials 1-4 is a powdered crystal material having a well-defined Debye-Scherrer X-ray diffraction pattern. By a "powdered" crystal material it is meant that the material is formed from some ten or more randomly oriented single crystals. For such materials, a collimated, monochromatic, incident X-ray beam 18 is diffracted in accordance with Braggs law to produce diffracted beams lying on the surface of several cones 22 as shown in FIG. 2(a). The cones 22 may emerge in all directions, forward (in the direction of the X-ray beam 18) and backward (in a direction opposite that of the X-ray beam 18). When the cones 22 are projected onto planes 26 and 28, the diffraction pattern includes one or more concentric rings 14 as shown in FIGS. 2(b) and 2(c). FIG. 2(b) depicts the backward plane 26, and FIG. 2(c) depicts the forward plane 28. The diffraction pattern (e.g., rings 14) formed on the forward plane 28 or the diffraction pattern (e.g., rings 14) formed on the backward plane 26, or both, may be used in the encoding method of the present invention.

The diffraction patterns may be detected using any known optical detectors 30 (e.g., a charge coupled device (CCD) detector, film, image plate detectors, among others) positioned at the planes 26 and 28. Such optical detectors 30 may have apertures 32 disposed therethrough for allowing passage of the incident X-ray beam 18 and the transmitted portion of X-ray beam 18 (indicated at 18').

Referring to FIG. 3, it is contemplated that any portion of the cones 22 may be used to form an X-ray diffraction pattern. For example, FIG. 3(a) depicts a Debye-Scherrer camera, in which an optical detector 30 (e.g., a charge coupled device (CCD) detector, film, image plate detectors, among others) is disposed concentrically around the identification element 8. FIG. 3(*b*) depicts the detector 30 in a straightened state. As can be seen in FIG. 3(*b*), the X-ray diffraction pattern captured by the detector 30 is a portion of the rings 14, which appear on the detector as arcs or "lines". All or part of the portion of the rings 14 may be used in the encoding method of the present invention.

Referring again to FIG. 1, combining one or more powdered crystal material in the binder material 5 will produce an element 8 with a composite X-ray diffraction pattern 13 made up of one or more well-defined rings 14 (or portions of rings 14), as shown in FIG. 1. Selection and omission of certain materials allow the combined X-ray diffraction pattern 13 of the optical identification element 8 to be encoded, with the presence or absence of each of the rings 14 (or portions of rings 14) indicating a binary "1" or "0" in the code 58, as indicated in FIGS. 4*a-c*. While FIGS. 1 and 4*a-c* show only five different codes, it will be appreciated that the four materials 1-4 in the example of FIG. 1 can be used to generate 16 different codes 58 by virtue of either their presence or absence. It is contemplated that the number of materials used is a function of the number of different codes needed to identify the item. For example, the use of 10 materials provides 1024 different codes, and N materials provides $2^N$ different codes. Advantageously, the present invention provides a labeling technique that allows for a large number of distinct codes.

While the code 58 is shown as a binary code, it is contemplated that higher order codes may be used. For example, by providing N coding identifiers, each having M distinguishable states, $M^N$ unique codes can be created. Where M=2 (e.g., the two states could be the presence or absence of the materials 1-4), the code 58 is the base 2 or binary code described above. In the case of M=3 (e.g., where the three states could be three distinguishable intensity levels for a range of inter atomic (D) spacings, the code 58 would be defined by a base 3 code. It is also contemplated that code 58 may be defined by analog coding methods; for example, the signature of each component of the entire composite spectrum 13 may be analyzed.

Figure 5:
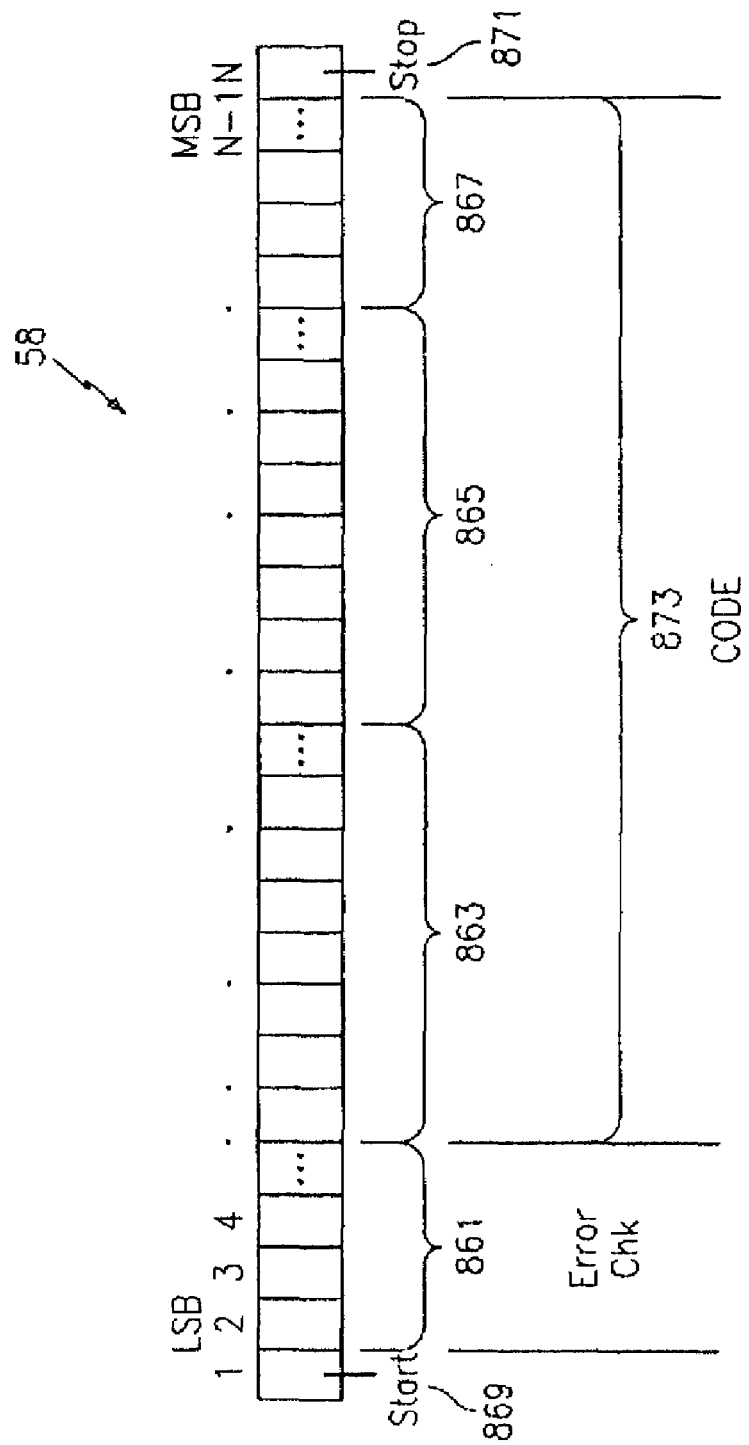
FIG. 5 shows a bit format for a code in an optical identification element of the present invention.

Referring to FIG. 5, the code 58 may be a simple code or may be a more complex code having many pieces of information located in the code 58. In addition, the code 58 may have checks within the code to ensure the code 58 is read correctly. It can be viewed as a serial digital message, word, or frame consisting of N bits.

In particular, there may be start and stop bits 869, 871, respectively. The start and stop bits may each take up more than one bit location if desired. In addition there may be an error check portion 861 of the message, such as a check sum or CRC (cyclic redundancy check) having a predetermined number of bits, and a code section 873 having a predetermined number of bits. The error check portion ensures that the code 8 which is obtained from the bead is accurate. Accordingly, having a large number of bits in the element 8 allows for greater statistical accuracy in the code 8 readout and decreases the likelihood of providing erroneous data. Accordingly, if a code 8 cannot be read without an error, no data from that code 8 will be provided, avoiding an erroneous result. Any known techniques for digital error checking for single or multi-bit errors may be used.

The code section 873 may be broken up into one or more groups of bits, for example, three bit groups 863,865,867, each bit group containing information about the bead itself or the item attached to the bead or how the bead is to be used, or other information. For example, the first bit group 863 may contain information regarding "identifying numbers", such as: lot number, quality control number, model number, serial number, inventory control number; the second bit group 865 may contain "type" information, such as: chemical or cell type, experiment type, item type, animal type; and the third bit group 867 may contain "date" information, such as: manufactured date, experiment date, creation date, initial tracking date. Any other bit groups, number of bit groups, or size of bit groups may be used if desired. Also, additional error or fault checking can be used if desired.

In particular, for a product manufacturing application, the code section 873 may have the serial number, the lot number, date of manufacture, etc. or have other information that identifies the item and/or information about the item. For a chemical or assay application, the code section 873 may have information about the chemical attached to the bead, the date and/or time of creation of the chemical or experiment, or other information of interest.

Figure 6A:
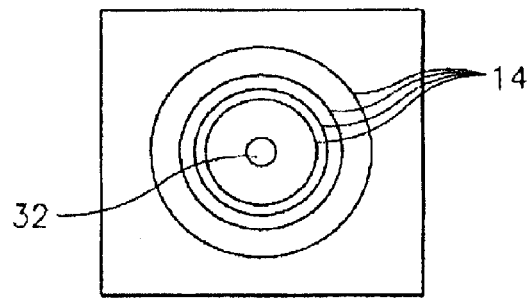
FIG. 6 illustration (a) shows an X-ray diffraction pattern for powdered aluminum, and illustration (b) is a plot of intensity and d spacing for various materials.
Figure 6B:
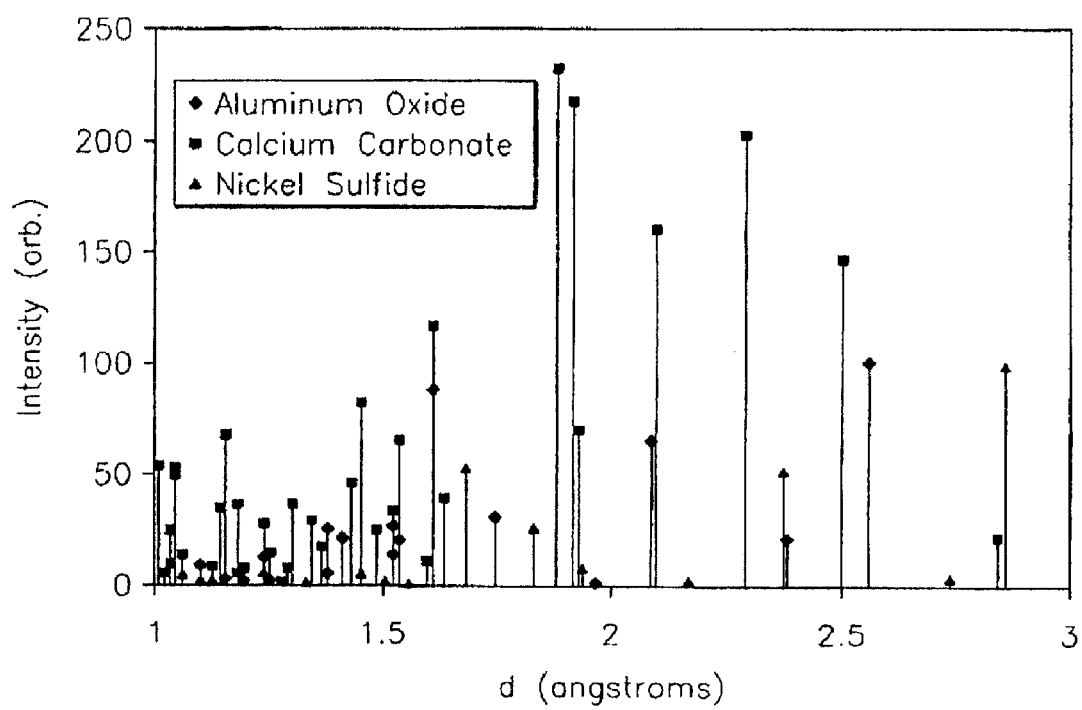

FIG. 6 illustration (a) shows an X-ray diffraction pattern for powdered aluminum, which comprises four rings 14. Other suitable materials include, for example, aluminum oxide, calcium carbonate, and nickel sulfide, as shown in FIG. 6 illustration (b).

Referring again to FIG. 1, the binder material 5 is preferably a material that does not diffract the X-ray beam 18 (FIGS. 2 and 3), or which diffracts the X-ray beam 18 in a known (i.e., filterable) manner. For example, the binder material 5 may be selected from glass, plastic, one or more polymers, and combinations including one or more of the foregoing. In other examples, the binder material 5 may be made of any one or more of various glasses, e.g., silica, phosphate glass, borosilicate glass, or other glasses, or made of glass and plastic, or solely plastic.

Figure 7:
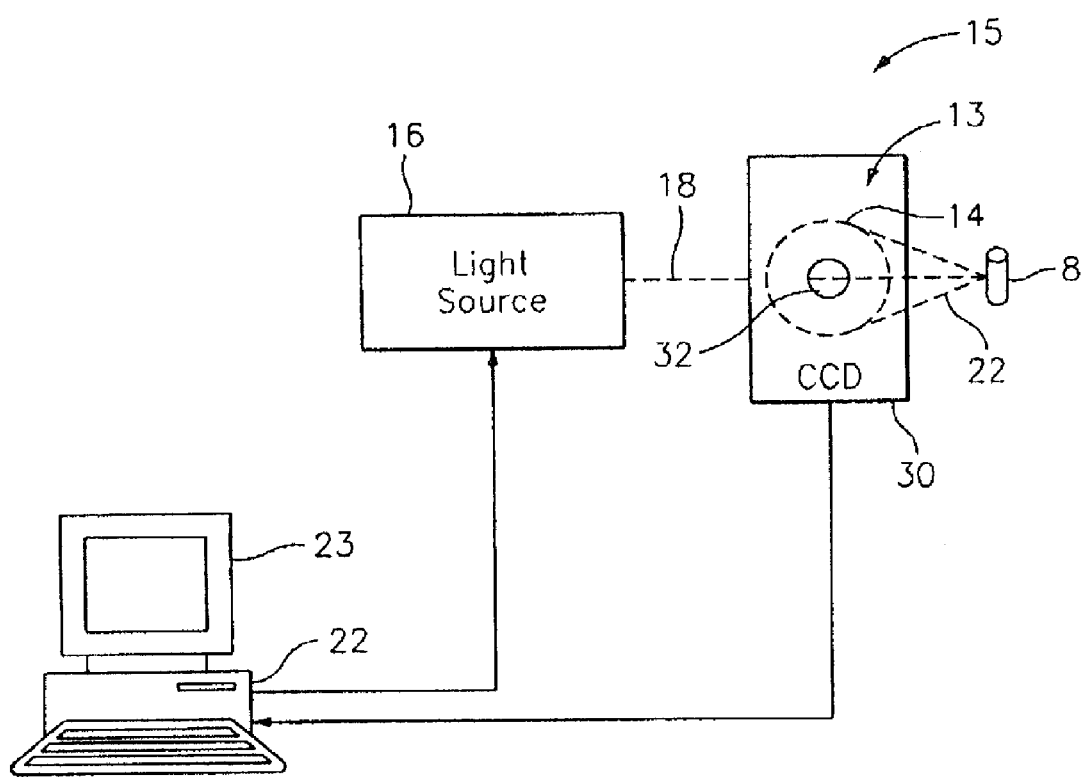
FIG. 7 is a schematic diagram of a system for identifying an item having one or more optical identification elements physically associated therewith in accordance with various embodiments of the present invention.

Referring to FIG. 7, a system for identifying an item having one or more optical identification elements 8 physically associated therewith is shown generally at 15. The system 15 has the necessary optics, electronics, software and/or firmware to perform the functions described herein. The system 15 may include any commercially available X-ray diffractometer.

Referring to FIGS. 1 and 7, the system 15 includes a light source 16, an optical detector 30, a computer 22, and an output device 23. The light source 16 provides a collimated, monochromatic X-ray beam 18, which may be triggered or otherwise controlled by the computer 22. The optical detector 30 (e.g., a multichannel charge-coupled device array) is situated to receive the composite X-ray diffraction pattern 13 produced by the illuminated optical identification element 8 and provide an output signal indicative of this composite X-ray diffraction pattern 13. In the embodiment shown, the optical detector 30 is arranged to receive only the back reflected portion of the composite X-ray diffraction pattern 13. As previously discussed, the optical detector 30 may be arranged to receive all or a portion of any part of the composite X-ray diffraction pattern 13. For example, the optical detector 30 may be arranged as described herein with reference to FIG. 2 or 3.

The computer 22 receives the output signal from the optical detector 30, decodes the composite X-ray diffraction pattern 13, and provides a binary or higher order code 58 indicative of the composite X-ray diffraction pattern 13. The decoding may be performed by identifying at least portions of unique Debye-Scherrer diffraction patterns in the composite X-ray diffraction pattern 13. A lookup table, database, or the like may then be used to determine the item associated with the code 58, and the name of the item may then be displayed on the output device 23.

Referring again to FIG. 1, the optical identification element 8 may be of any convenient shape. For example, the optical identification element 8 may be shaped as a bead, such as a microbead (or microelement, micro-particle, or encoded particle) having at least one dimension of less than about 1000 microns or a macrobead having at least one dimension of greater than about 1000 millimeters. Alternatively, the binder material may be in the form of a thread or fiber or may be in the form of a paint or coating.

Figure 11:
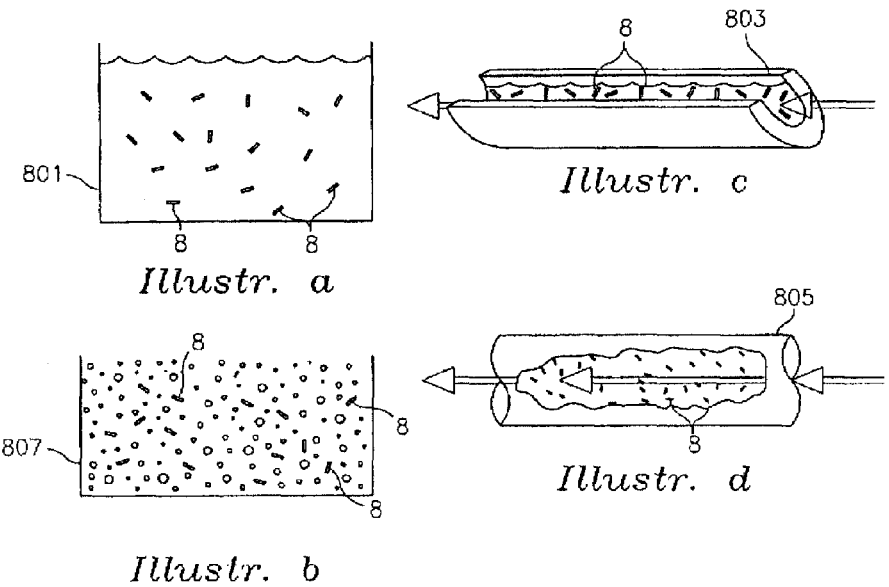
FIG. 11, illustrations (a)-(d) show fluids or powders that can be labeled with an optical identification element of the present invention.
Figure 12:
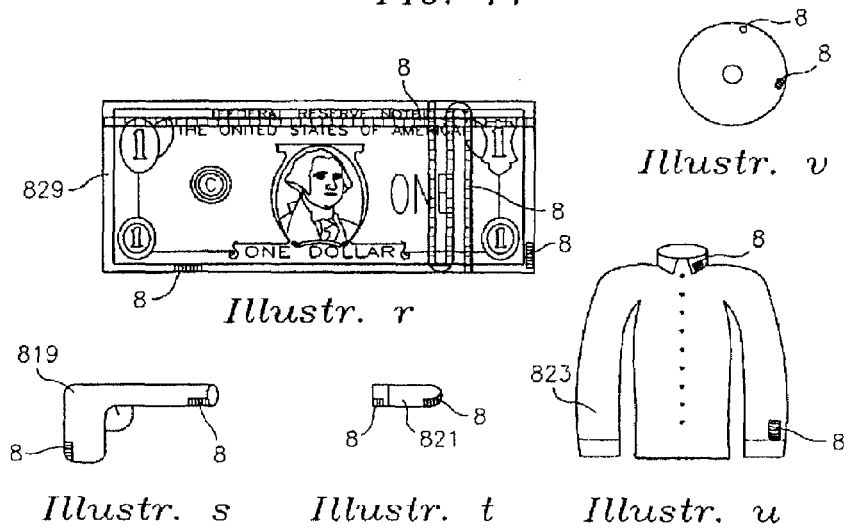
FIG. 12, illustrations (a)-(v) show various other items that can be labeled with an optical identification element of the present invention.
Figure 12:
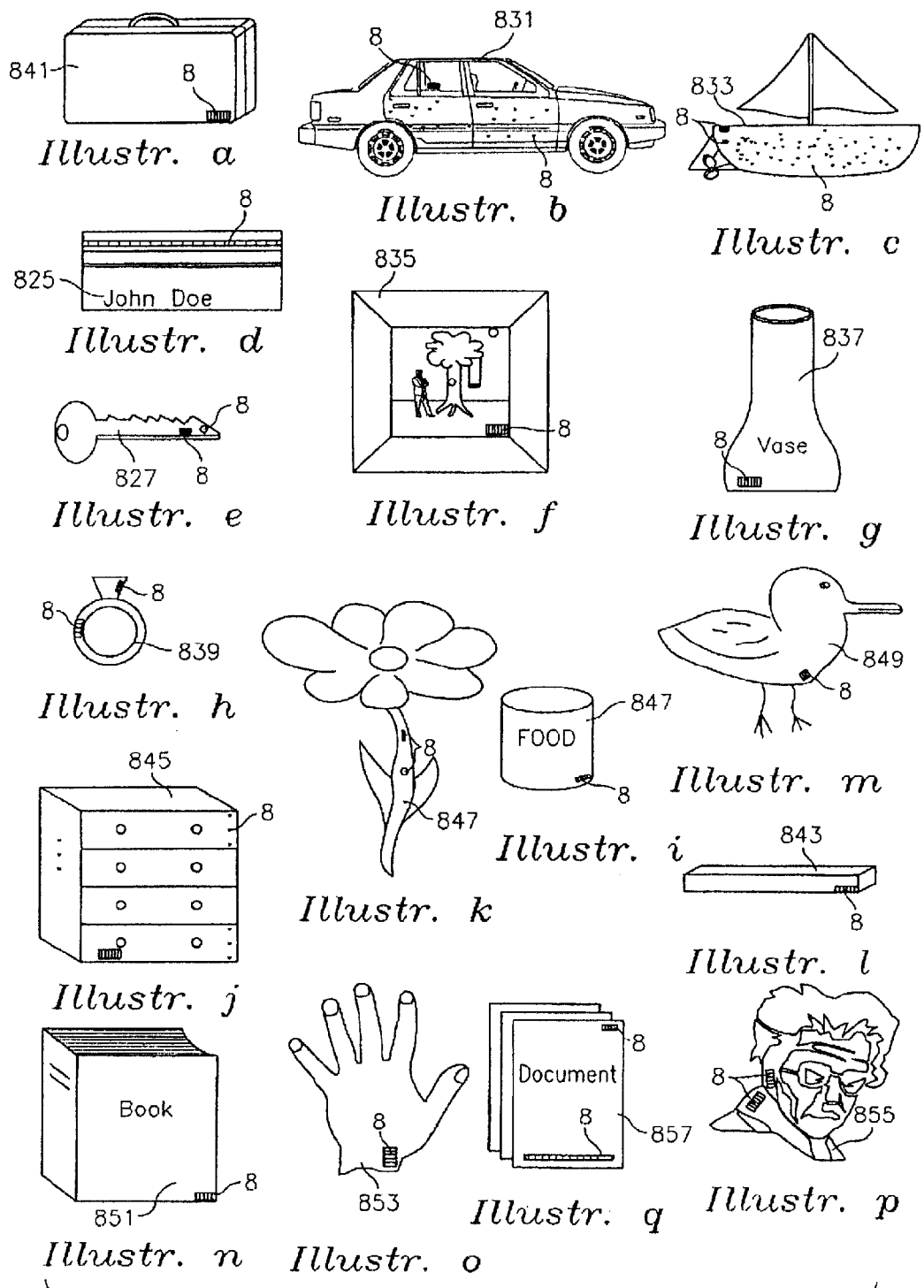
Figure 13A:
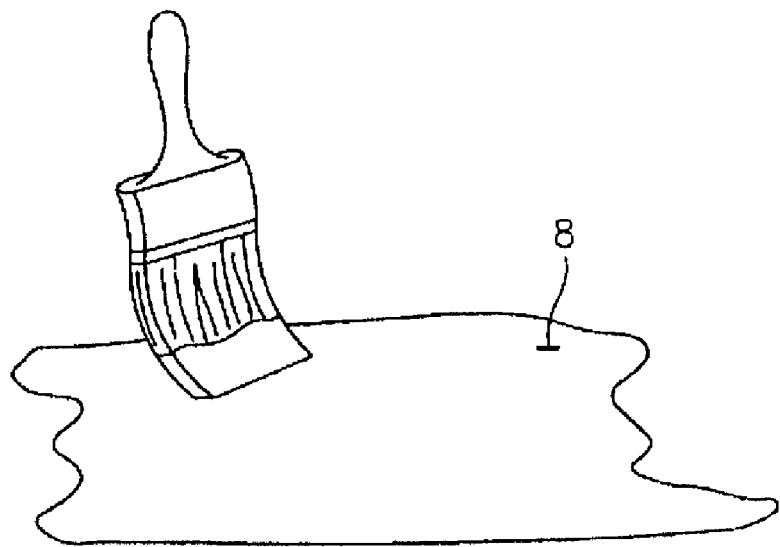
FIG. 13 illustrations (a) and (b) depict the optical identification element being applied as a paint or powder coating.
Figure 13B:
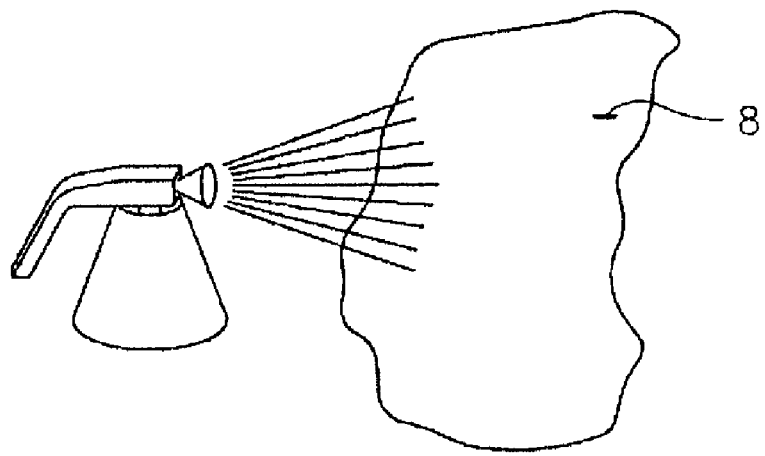
Figure 14:
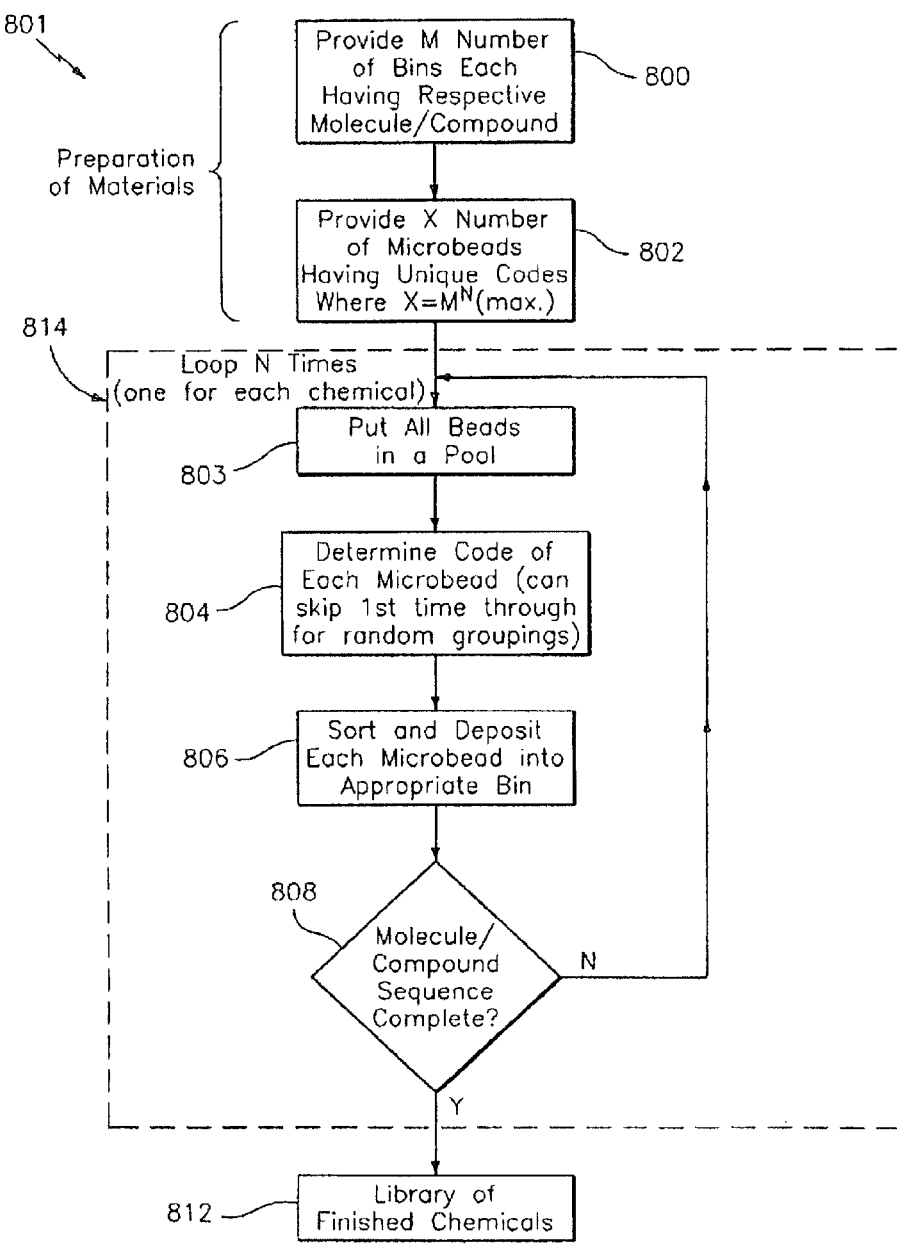
FIG. 14 is a flow chart for a chemical split and pool synthesis apparatus in accordance with various embodiments of the present invention.

As shown in FIGS. 8-12, the encoded element 8 may be used to label any desired item, such as large or small objects, products, solids, powders, liquids, gases, plants, pharmaceuticals (drugs), minerals, and/or animals, or any combination of one or more thereof. The label may be used for many different purposes, such as for sorting, tracking, identification, verification, authentication, anti-theft/anti-counterfeit, security/anti-terrorism, or for other purposes. In a manufacturing environment, the elements 8 may be used to track inventory for production information or sales of goods/products. As shown in FIG. 13, the encoded element 8 may be in the form of a paint or powder coating. The paint or powder coating can be applied to virtually any surface. For example, the paint or powder coating may be applied to a vehicle such as a boat or car, or a container transported by ship.

Also, the X-ray diffraction material or substances of the present invention may be incorporated into an ink, paint, powder or any other printing substance that allows printed documents to be uniquely identified by the X-ray diffraction pattern emitted in response to the incident X-ray. In that case, the text itself would emit a predetermined diffraction pattern that uniquely identifies the document. Such material could also be incorporated into the paper, document, or package making process, e.g., the pulp or the coatings, that uniquely identifies the product made.

For any of the labeled items described herein, the encoded elements 8 may be tiny discrete microbeads (0.01 micrometers to 1000 micrometers long) embedded into the surface of the item or the encoded element 8 may be a long strand of glass or plastic fiber that is woven, inserted, impressed, or injected into the item being labeled. Alternatively, in the appropriate cases, the materials 1-4 may be impressed directly into the material. In any case, the properties of the encoded element 8 do not change. For labeled items that are pliable, bendable, or flexible, the element 8 may be made of a bendable material, such as a polymer or plastic. Also, if the item material is soft or compliant the beads may be pressed, pushed, hammered or shot into the material.

In general, the encoded elements 8 may be used to label any products or components within a product and may be used for product manufacturing/production identification.

Figure 8:
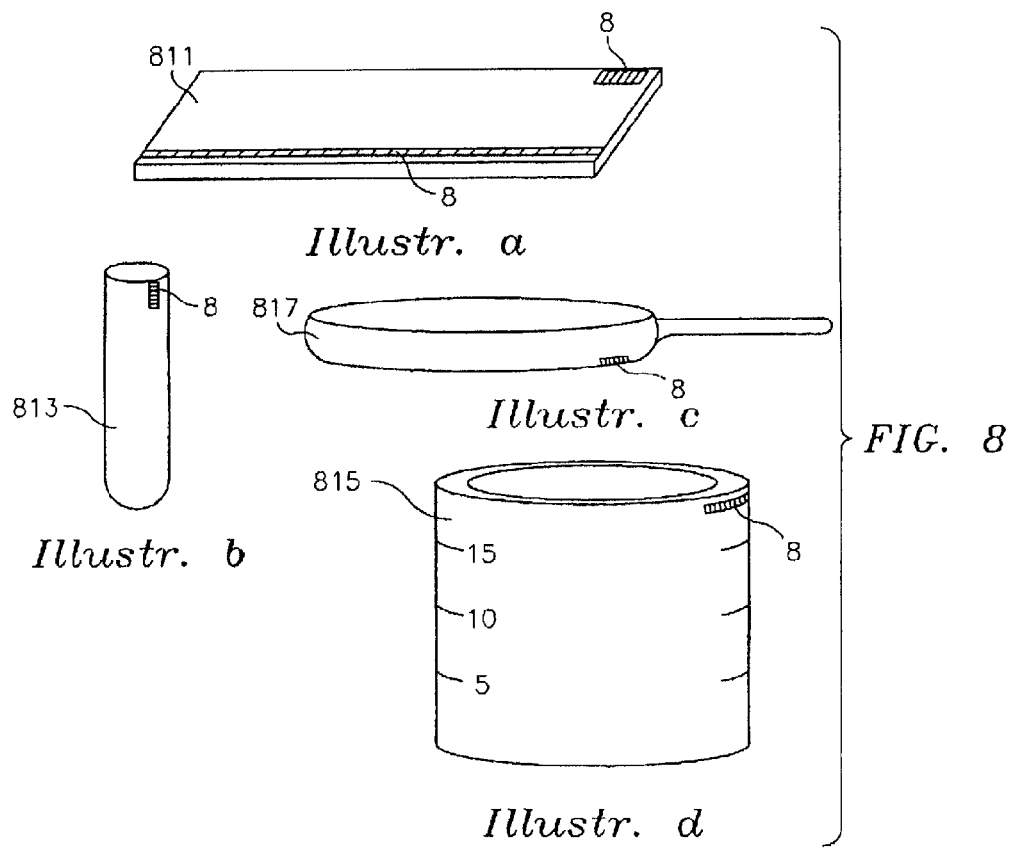
FIG. 8 illustrations (a)-(d) show various transparent items that can be labeled with an optical identification element of the present invention.

Referring to FIG. 8, illustrations (a)-(d), encoded elements 8 may be used to label glass or plastic items, such as microscope slides 811, test tubes 813, beakers 815, cookware 817, storage containers and/or covers, multi-well plates, microwell plates, plastic bags, windshields, windows, glasses, contact lenses, other lenses, optical components, tape, bottles, displays, display cases, watch faces, mirrors, sample or pietri dishes, or any other item made of a material that is transparent or substantially transparent to the incident X-ray 24 and reflected X-ray 27 used for read the code in the encoded elements 8. The invention may be used to identify such glass or plastic items by embedding the materials 1-4 directly into the item or by embedding into or otherwise attaching the encoded elements 8 to the item. In the case where the materials 1-4 are embedded directly into the item, the material forming the item is the binder material 5 and is preferably a material that does not affect the X-ray diffraction pattern provided by the materials 1-4, or which affects the X-ray diffraction pattern in a known (i.e., filterable) manner.

Figure 9:
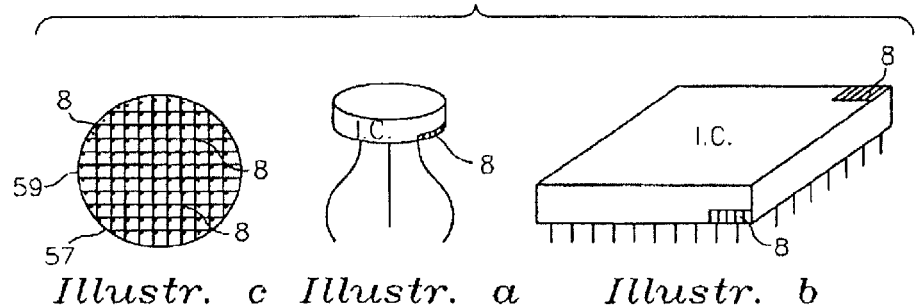
FIG. 9, illustrations (a)-(c) show various integrated circuits or silicon wafers, that can be labeled with an optical identification element of the present invention.

Referring to FIG. 9, illustrations (a) and (b), the encoded elements 8 may be used to label micron size products, such as, microcircuits computer chips, integrated circuits (IC's), or other small products or portions thereof. Referring to FIG. 9, illustration (c), the elements 8 may also be used to label silicon wafers 59 or small portions or regions 57 thereof before being cut into small devices or microcircuits.

Figure 10:
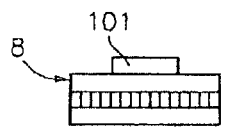
FIG. 10 shows a cell or the like disposed on an optical identification element.

Referring to FIG. 10, the elements 8 may be used to label any single or multiple cells 101 that are attached to or otherwise disposed on the element 8. The cells 101 may include: molecules, particles, elements, compounds, organisms, atoms, chemicals, acids, bases, nucleic acids, chemical libraries, DNA, polynucleotides, oligomers, RNA, proteins, peptides, polymers, hydrocarbons, or other cells. The cells 101 may be alive or dead, organic or inorganic, and may be individual or groups or chains of cells and may change or mutate over time.

Referring to FIG. 11, illustrations, (a)-(d), the encoded elements 8 may be used to label a liquid or liquid products located in a container 801 or in an open or closed flowing pipe or conduit 803, 805 respectively. In that case, the elements 8 are mixed with the liquid. In addition, the elements 8 may also be used to label powders, such as powdered detergent, dirt, pulverized coal, gunpowder, anthrax, or any other powders located in a container 807, or in an open or closed flowing pipe or conduit 803, 805, respectively. Also, the elements 8 may be used to label or identify any combination of fluids (liquids and/or gases) and/or powders. Also, the elements 8 may be used to label gases, such as gases in containers or gases flowing in a pipe or conduit, or gaseous by-products of reactions, such as combustion exhaust or other exhaust. Also, the elements 8 may be used to label liquid particles or droplets in gas, such as steam. The elements 8 may be used to track the flow of a liquid, powder, gas, etc. in an industrial plant to determine where the liquid is flowing or has flown.

The elements 8 may be removed from a fluid, powder and/or gas solution or mixture other material by electromagnetic attraction (if the elements 8 are electro-magnetic), skimmed off the surface (if the elements 8 are less dense than the solution, i.e., buoyant or semi-buoyant), or from settling to the bottom of a container (if the elements 8 are more dense than the solution), or by filtering the solution with a strainer or filter.

The elements 8 can placed in a fluid or powder and the fluid or powder is used for labeling an item. For example, the elements 8 may be mixed with paint (or other adhesive fluid) and sprayed on an item, such as a car or boat (see FIG. 12, illustrations (b) and (c)) or any other item that can be sprayed or painted. The same may be done with a dry powder that is sprayed on a newly painted or otherwise adhesive surface, or with an adhesive powder that is sprayed on a dry, or painted or adhesive surface.

Referring to FIG. 12, illustrations (a), (b), (c), (f), (g), and (h), in particular, the encoded elements 8 may be used to label large and/or valuable items such as cases 841 (e.g., suitcases, briefcases, garment bags, and the like), cars 831, boats 833, paintings 835, china 837, jewelry 839, and the like. Also, the elements 8 may be used as a way of putting the vehicle identification number (VIN) or other similar identification information in a hidden location and/or in many locations on an item that can only be read by the proper equipment.

Referring to FIG. 12, illustrations (d), (e), and (r), the encoded elements 8 may also be used to label currency 829, coins, bills, or credit cards. Also, the elements 8 may be used an alternative or addition to magnetic strips currently used on many types of cards 825, e.g., access cards, key cards, ID cards, debit cards, credit cards, and the like. In addition, the elements 8 may be used as part of a key 827.

Referring to FIG. 12, illustration (i), the elements 8 may be used to label food containers 847 and the like.

Referring to FIG. 12, illustrations (j) and (l), the elements 8 may be used to label building materials 843, e.g., wood, pressboard, composite boards (e.g., made of wood, plastic, and/or metal particles), wallboard, wallpaper, molding, tiles and the like or other building materials. Similarly, the elements 8 may be used to label furniture or other home or office furnishings 845.

Referring to FIG. 12, illustrations (m), (o), and (p), the encoded elements 8 may be used to label any animals 849, creatures, people/humans 855, and/or plants, or parts thereof 853. Such a label could be used in addition to or instead of fingerprints, retina scans, DNA or other identification techniques or labels.

Referring to FIG. 12, illustrations (n) and (q), the encoded elements 8 may be used to label documents 857, books 851, and/or packages.

Referring to FIG. 12, illustrations (s) and (t), the encoded elements 8 may be used to label weapons, ammunition, explosive devices, guns 819, artillery, bullets 821, mortar, grenades, missiles, torpedoes, projectiles, fireworks, bombs, spacecraft, aircraft, satellites, jet engines, submarines and tanks.

Referring to FIG. 12, illustration (u), the encoded elements 8 may be used to label clothing 823, garments, uniforms, linens, leather, footwear, headgear, or textiles.

Referring to FIG. 12, illustration (v), the encoded elements 8 may be used to label storage media, such as compact discs and digital video discs (DVD's), or any other devices that uses light to read information, video or audio tapes, disc drives, and the like.

Referring to FIG. 13, the optical elements described herein may be used to synthesize chemicals in a known split and pool synthesis technique, such as that described in U.S. patent application Ser. No. 10/661,254, filed Sep. 12, 2003, which is incorporated by reference herein in its entirety. In particular, a known split and pool bead based synthesis process 801, may be performed starting with a step 800 where a predetermined number M of compounds or chemicals are provided each in a separate bin or container and at step 802 where a predetermined number X of microbeads 8 are provided each having its own unique code. Steps 800, 802 are material preparation steps and can be done in either order. After the materials are prepared, a step 803 combines or pools all the beads together. Then, a step 804 determines the code for each microbead 8. This step can be skipped on the first time through the process if it is desired to randomly split up the beads into groups, i.e., to not split the groups up by code on bead during the first run. Next a step 806 sorts the beads based on its code and deposits the bead into the appropriate bin for the chemical to be added to the bead.

Next, a step 808 tests to see if the chemical synthesis is complete for each bead. If not the process goes back to step 803 where the remaining beads are recombined or re-pooled and the process starts again. The loop 814 repeats a predetermined number of times N, where each time through the loop 814 another chemical is added to each of the beads. If certain beads are to have fewer chemicals than others, then certain beads will drop out of the process before others. When the step 808 concludes that one or more beads have completed their synthesis process, a step 812 logs the completion of that bead and the remainder of the beads continue until all desired chemicals have synthesized on the beads.

For example, for M=4 compounds and N=10 chemicals to add to each bead, the total number of different codes needed would be 1,048,576 or $M^N$ and if there will be only one bead with each desired chemical (i.e., no redundancy), then the number of beads X would also be $M^N$=1,048,576.

Figure 15:
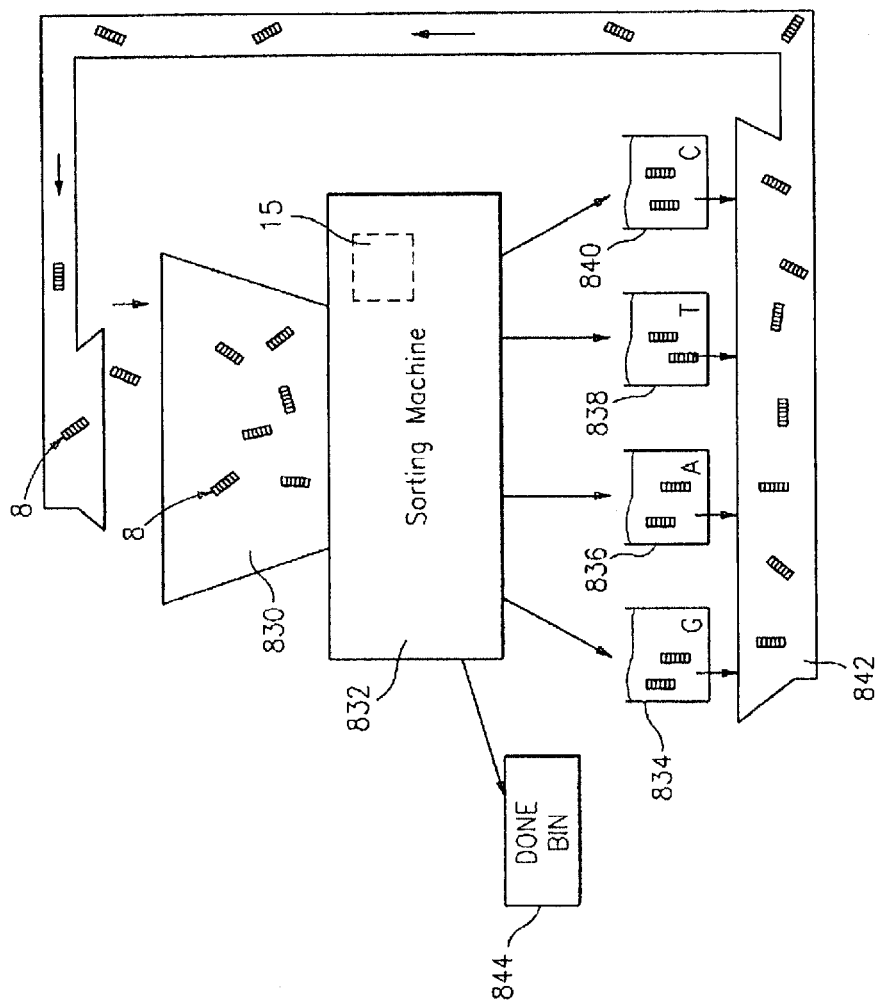
FIG. 15 is a diagram of a chemical split and pool synthesis apparatus in accordance with various embodiments of the present invention.
Figure 16:
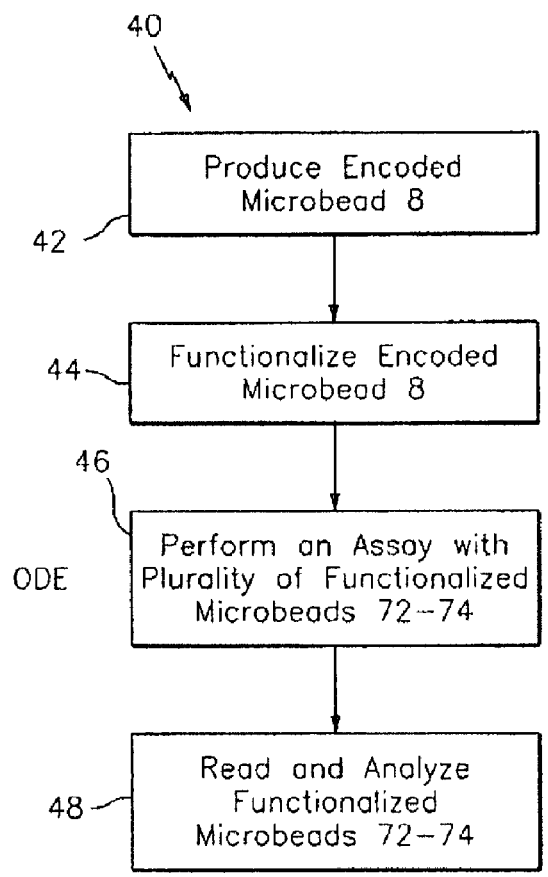
FIG. 16 is a flow chart of a method of attaching a substance to an optical identification element, performing an assay and analyzing the optical identification element in accordance with various embodiments of the present invention.

Referring to FIG. 15, an automated synthesis machine is shown for synthesizing a chemical having four different possible compounds or cells or molecules (e.g., GCAT for a DNA synthesis), where a main bin 830 receives or pools all the beads 8 and provides the beads 8 to a sorting machine 832, which performs the sorting step 806 in the loop 814. The sorting may be accomplished using the system 15 described herein to identify the beads. In addition the machine 832 deposits the beads in the proper bins 834, 836, 838, 840, having the bases G,C,A,T, respectively. Any other four chemicals can be used if desired. Once the specific base has been attached to a bead it is dropped or placed in a device which transports the beads back into the main bin 830 for resorting by the machine 832. When synthesis has been completed on a given bead the machine deposits the completed bead in a done bin 844.

If it is desired to produce multiple of the same chemical on separate beads this can be done by having multiple beads with the same code, or presetting certain groups of codes to have the same chemical composition. In that case, each of these beads may go to the same bins in the same order as a group.

The present invention may be used with any known combinatorial chemistry, chemical synthesis process, or synthesizing labeled combinatorial chemistry libraries, and are especially adaptable to solid phase synthesis, for example: U.S. Pat. No., 6,417,010, "Methods and Apparatus for Synthesizing Labeled Combinatorial Chemistry Libraries", U.S. Pat. No. 6,558,904 entitled "Method for producing structured, self-organized molecular monolayers of individual molecular species, in particular substance libraries"; U.S. Pat. No. 6,541,276 entitled "Methods for solid-phase synthesis of hydroxylamine compounds and derivatives and combinatorial libraries thereof"; U.S. Pat. No. 6,541,211 "Apparatus and method for synthesizing combinational libraries"; U.S. Pat. No. 6,528,324 entitled "Apparatus for pre-determined mass sorting of positional-encoded solid phase synthesis supports"; U.S. Pat. No. 6,506,558 entitled "Very large scale immobilized polymer synthesis"; U.S. Pat. No. 6,495,539 entitled "B-lactam-like chaperone inhibitors"; U.S. Pat. No. 6,468,740 entitled "Cyclic and substituted immobilized molecular synthesis"; U.S. Pat. No. 6,417,010 entitled "Methods and apparatus for synthesizing labeled combinatorial chemistry libraries; U.S. Pat. No. 6,410,643 entitled "Solid phase synthesis method and reagent"; U.S. Pat. No. 6,410,342 entitled "Method and apparatus for controlled photoelution"; U.S. Pat. No. 6,387,636 entitled "Method of shielding biosynthesis reactions from the ambient environment on an array"; U.S. Pat. No. 6,372,885 entitled "Solid-phase technology for the preparation of amides"; U.S. Pat. No. 6,368,874 entitled "Methods for hard-tagging an encoded synthetic library"; U.S. Pat. No. 6,362,009 entitled "Solid phase synthesis of heterocycles"; U.S. Pat. No. 6,346,423 entitled "Methods and compositions for producing biopolymeric arrays"; U.S. Pat. No. 6,329,210 entitled "Method and apparatus for high volume polymer synthesis"; U.S. Pat. No. 6,294,694 entitled "Matrix metalloproteinase inhibitors and method of using same"; U.S. Pat. No. 6,274,385 entitled "Attached tags for use in combinatorial chemistry synthesis"; U.S. Pat. No. 6,265,228 entitled "Process for preparing combinatorial amide alcohol libraries"; U.S. Pat. No. 6,251,595 entitled "Methods and devices for carrying out chemical reactions"; U.S. Pat. No. 6,127,190 entitled "Method for producing combinatorial libraries having a predetermined frequency of each species of test compound"; U.S. Pat. No. 5,929,208 entitled "Methods for electronic synthesis of polymers"; U.S. Pat. No. 5,886,186 entitled "Synthesis of substituted N-heteroaromatic compounds and methods of use thereof"; U.S. Pat. No. 5,885,837 entitled "Very large scale immobilized polymer synthesis using mechanically directed flow paths"; U.S. Pat. No. 5,859,191 entitled "Method for the site-specific modification of peptide alpha amines"; U.S. Pat. No. 5,763,263 entitled "Method and apparatus for producing position addressable combinatorial libraries"; U.S. Pat. No. 5,712,171 entitled "Method of generating a plurality of chemical compounds in a spatially arranged array"; U.S. Pat. No. 5,690,894 entitled "High density array fabrication and readout method for a fiber optic biosensor"; U.S. Pat. No. 5,545,568 entitled "Solid phase and combinatorial synthesis of compounds on a solid support"; U.S. Pat. No. 5,545,531 entitled "Methods for making a device for concurrently processing multiple biological chip assays"; U.S. Pat. No. 5,539,083 entitled "Peptide nucleic acid combinatorial libraries and improved methods of synthesis"; U.S. Pat. No. 5,384,261 entitled "Very large scale immobilized polymer synthesis using mechanically directed flow paths"; U.S. Pat. No. 5,288,514 entitled "Solid phase and combinatorial synthesis of benzodiazepine compounds on a solid support"; U.S. Pat. No. 5,264,563 entitled "Process for synthesizing oligonucleotides with random codons"; U.S. Pat. No. 5,010,175 entitled "General method for producing and selecting peptides with specific properties"; U.S. Pat. No. 6,465,192 entitled "Compounds and methods for the inhibition of protein-protein interactions"; U.S. Pat. No. 6,440,669 entitled "Methods for applying small volumes of reagents"; U.S. Pat. No. 6,406,844 entitled "Very large scale immobilized polymer synthesis"; U.S. Pat. No. 6,329,010 entitled "Method and apparatus for high volume polymer synthesis"; U.S. Pat. No. 6,316,623 entitled "Ethylenediamine compound libraries"; U.S. Pat. No. 5,780,241 entitled "Complex chemical libraries"; U.S. Pat. No. 5,712,171 entitled "Method of generating a plurality of chemical compounds in a spatially arranged array"; U.S. Pat. No. 5,593,853 entitled "Generation and screening of synthetic drug libraries"; U.S. Pat. No. 6,569,631 entitled "Microplate thermal shift assay for ligand development using 5-(4"dimethylaminophenyl)-2-(4'-phenyl)oxazole derivative fluorescent dyes"; U.S. Pat. No. 6,503,759 entitled "Complex combinatorial chemical libraries encoded with tags"; U.S. Pat. No. 6,492,125 entitled "Method to assess library X library interactions"; U.S. Pat. No. 6,457,807 entitled "Mass-based encoding and qualitative analysis of combinatorial libraries"; U.S. Pat. No. 6,455,263 entitled "Small molecule library screening using FACS"; U.S. Pat. No. 6,096,496 entitled "Supports incorporating vertical cavity emitting lasers and tracking apparatus for use in combinatorial synthesis"; U.S. Pat. No. 5,770,455 entitled "Methods and apparatus for synthesizing labeled combiatorial chemistry libraries"; U.S. Pat. No. 5,751,629 entitled "Remotely programmable matrices with memories"; U.S. Pat. No. 6,537,504 "Method and apparatus for concurrent and sequential multi-step reactions for producing a plurality of different chemical compounds"; U.S. Pat. No. 6,468,806 "Potential masking systems and methods for combinatorial library synthesis"; U.S. Pat. No. 6,429,027 "Composite arrays utilizing microspheres"; U.S. Pat. No. 6,420,169 "Apparatus for forming polynucleotides or polypeptides"; U.S. Pat. No. 6,448,443 "Synthesis of combinatorial libraries of compounds reminiscent of natural products"; U.S. Pat. No. 5,840,485 "Topologically segregated, encoded solid phase libraries".

Referring to FIGS. 16-21, the optical identification element (or microbead) 8 may be functionalized by coating or attaching a desired probe 76, such as a compound, chemical or molecule, as described in U.S. patent application Ser. No. 10/661,031 filed Sep. 12, 2003, which is incorporated by reference herein in its entirety. The probe 76 is then used in an assay as an attractant for certain complimentary compounds, chemicals or molecules, otherwise known as a "target" analyte 52-54 (see FIG. 19). This capability to uniquely encode a large number of microbeads 8 with a corresponding unique probe 76 attached thereto enables these functionalized microbeads 72 to be mixed with unknown "target" analytes 52-54 to perform a multiplexed experiment. The procedure 40 for performing such a multiplexed assay or experiment includes the steps of producing (step 42) the encoded optical identification element (microbead) 8, as described hereinbefore, and functionalizing (step 44) the substrate 10 of the microbead 8 by coating/depositing/growing it with a probe 76 that will react in a predetermined way with "target" analytes 52-54. An assay is then performed (step 46) with a plurality of functionalized microbeads 72 with different identification codes 58 at the same time. In step 48, the fluorescence of the functionalized microbeads 72 is analyzed, and the functionalized microbead 72 is read to determine the code 58 thereof to thereby determine which "target" analytes 52-54 are present in the solution 60.

Figures 17, 18:
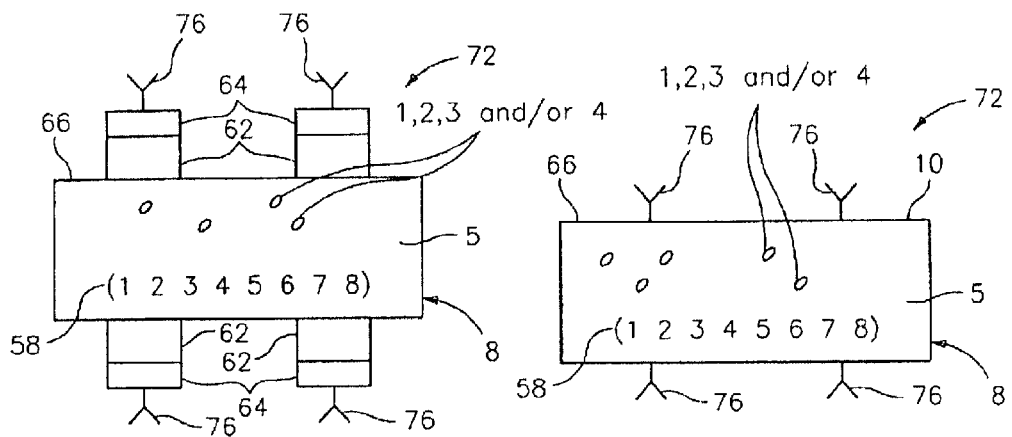
FIG. 17 is a side view of an optical identification element having a substance attached to the outer surface thereof in accordance with various embodiments of the present invention.
FIG. 18 is a side view of an optical identification element having a substance attached to the outer surface thereof, in accordance with various embodiments of the present invention.
Figure 19:
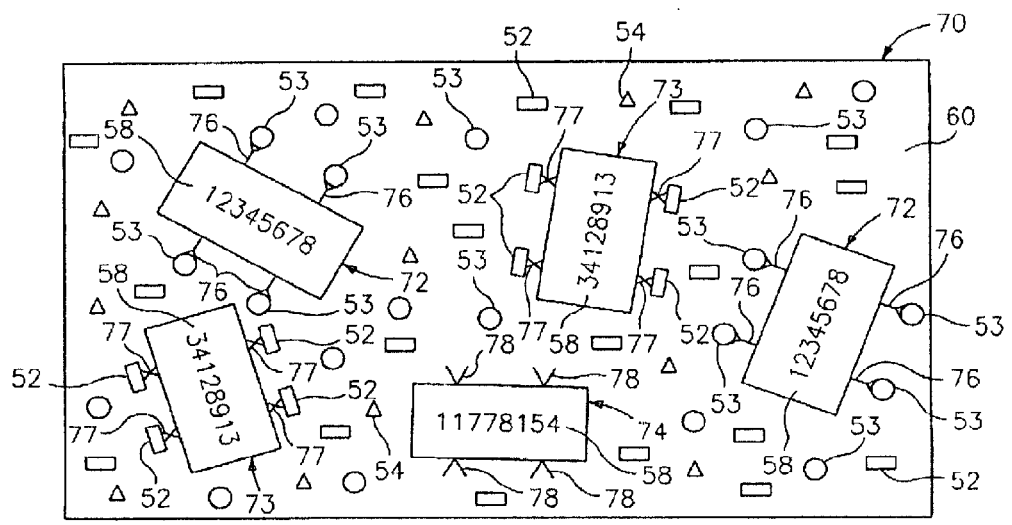
FIG. 19 is a schematic view of a plurality of optical identification elements having different identification or codes and coated with different probe substances disposed in a cell with a plurality of test substances, in accordance with various embodiments of the present invention.

In FIGS. 17 and 18, a functionalized microbead 72 is shown, wherein the substrate 10 of the microbead 8 is coated with a probe 76 and used in an assay or as an attractant for certain "target" analytes 52-54 (see FIG. 19). In one embodiment shown in FIG. 17, the microbead 8 is coated with a linker molecule or complex 62 as is known in the art. A molecular group 64 is attached to the probe 76 to enable the probe to be bonded to the linker molecule or complex 62, and thus to the microbead 8 to form the functionalized microbead 72. The probe 76 may include one of an Oligonucleitides (oligos), antibodies, peptides, amino acid strings, cDNA, RNA, chemicals, nucleic acid oliomers, polymers, biological cells, or proteins. For example, the probe 76 may comprise a single strand of DNA (or portion thereof) and the "target" analyte 52-54 comprises at least one unknown single strand of DNA, wherein each different "target" analyte has a different DNA sequence.

In some instances as shown in FIG. 18, the probe 76 may be attached directly to the substrate 10 of the microbead 8, or directly synthesized (or grown) thereon, such as via phosphoramidite chemistry. Examples of surface chemistry for the functionalized microbeads 72 include Streptavidin/biotinylated oligos and Aldehyde/amine modified oligos. Further, the microbead may be coated with a blocker of non-specific binding (e.g., salmon sperm DNA) to prevent bonding of analytes 52-54 (e.g. DNA) to the non-functionalized surface 66 of the functionalized microbeads 72.

Referring to FIG. 19, an assay is performed by adding a solution 60 of different types of "target" analytes 52-54 into a cell or container 70 having a plurality of functionalized microbeads 72-74 disposed therein. As discussed in step 46 of FIG. 16, the functionalized microbeads 72-74 placed in the cell 70 have different identification codes 58 that correspond to unique probes 76-78 bonded thereto. For example, all functionalized microbeads 72 disposed within the cell 70 having an identification code of 12345678 is coated with a unique probe 76. All functionalized microbeads 73 disposed within the cell 72 having an identification code of 34128913 is coated with a unique probe 77. All functionalized microbeads 77 disposed within the cell 70 having an identification code of 11778154 is coated with a unique probe 78.

The "target" analytes 52-54 within the solution 60 are then mixed with the functionalized microbeads 72-74. During the mixing of the "target" analytes 52-54 and the functionalized microbeads 72-74, the "target" analytes attach to the complementary probes 76-78, as shown for functionalized microbeads 72,73 having codes 12345678 and 34128913. Specifically, as shown in FIG. 19, "target" analytes 53 bonded with probes 76 of the functionalized microbeads 72 having the code 12345678, and "target" analytes 52 bonded with probes 77 of the functionalized microbeads 73 having the code 34128913. On the other hand, "target" analytes 54 did not bond with any probes, and not "target" analytes 52-54 in the solution 60 bonded with probes 78 of the functionalized microbeads 74 having-the-code 11778154. Consequently, knowing which "target" analytes attach to which probes along with the capability of identifying each probe by the encoded microbead, the results of the assay would show that the unknown "target" analytes in the solution 60 includes "target" analytes 53, 54, as will be described in further detail.

For example as discussed hereinbefore, each coded functionalized microbead 72-74 has a unique probe 76-78, respectively bonded thereto, such as a portion of a single strand of DNA. Similarly, the "target" analytes 52-54 comprise a plurality of unknown and unique single strands of DNA. These "target" analytes 52-54 are also processed with a fluorescent, such as dyeing, such that the test molecules illuminate. As will be discussed hereinafter, the fluorescence of the "target" analytes provide the means to identify, which functionalized microbeads 72-74 have a "target" analyte attached thereto.

Figure 20:
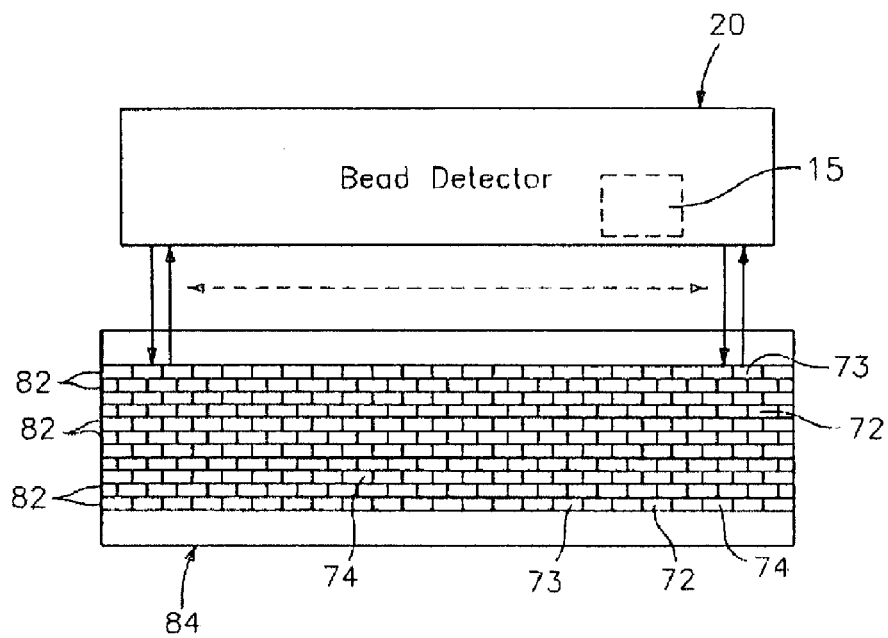
FIG. 20 is a schematic view of plurality of optical identification elements after the performance of an assay, aligned in a plurality of grooves, disposed on a substrate, and a bead detector that scans each optical identification element for determining the code and fluorescence of each optical identification element, in accordance with various embodiments of the present invention.

Once the reaction or combining is complete, the functionalized microbeads 72-74 are rinsed off with a saline solution to clean off the uncombined "target" analytes 52-54. As shown in FIG. 20, the functionalized microbeads 72-74 may be placed in a tray 84 with grooves 82 to allow the functionalized microbeads to be aligned in a predetermined direction, such as that described in U.S. patent application Ser. Nos. 10/661,234, 10/645,689, 10/661,836, 60/546,435, 60/609,583, and 60/610,910, which are all incorporated herein by reference. The grooves 82 may have holes (not shown) that provide suction to keep the functionalized microbeads in position. Once aligned in the tray 84, the functionalized microbeads 52-54 are individually scanned and analyzed by the bead detector 20, which includes one or more systems 15.

Figure 21:
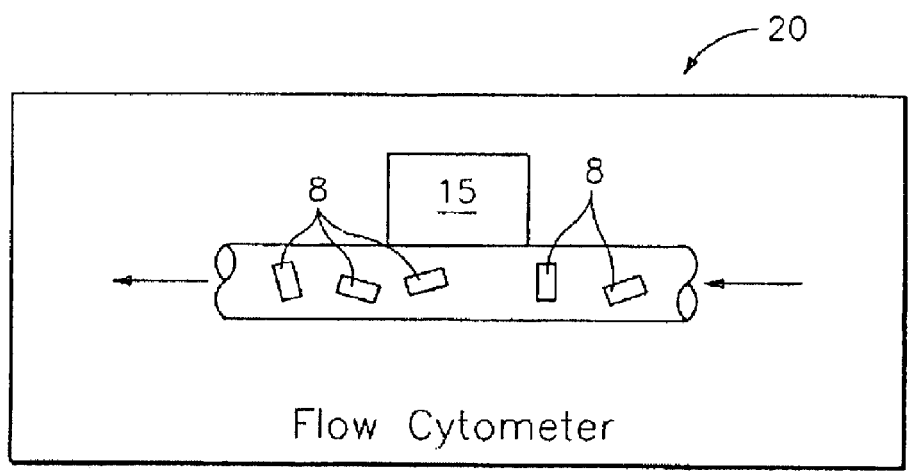
FIG. 21 is a schematic view of a flow cytometer including a system for identifying an item having one or more optical identification elements physically associated therewith in accordance with various embodiments of the present invention.

Alternatively, the functionalized microbeads 72-74 may be scanned and analyzed in a flow cytometer 20 including one or more systems 15 as depicted in FIG. 21.

Figure 22:
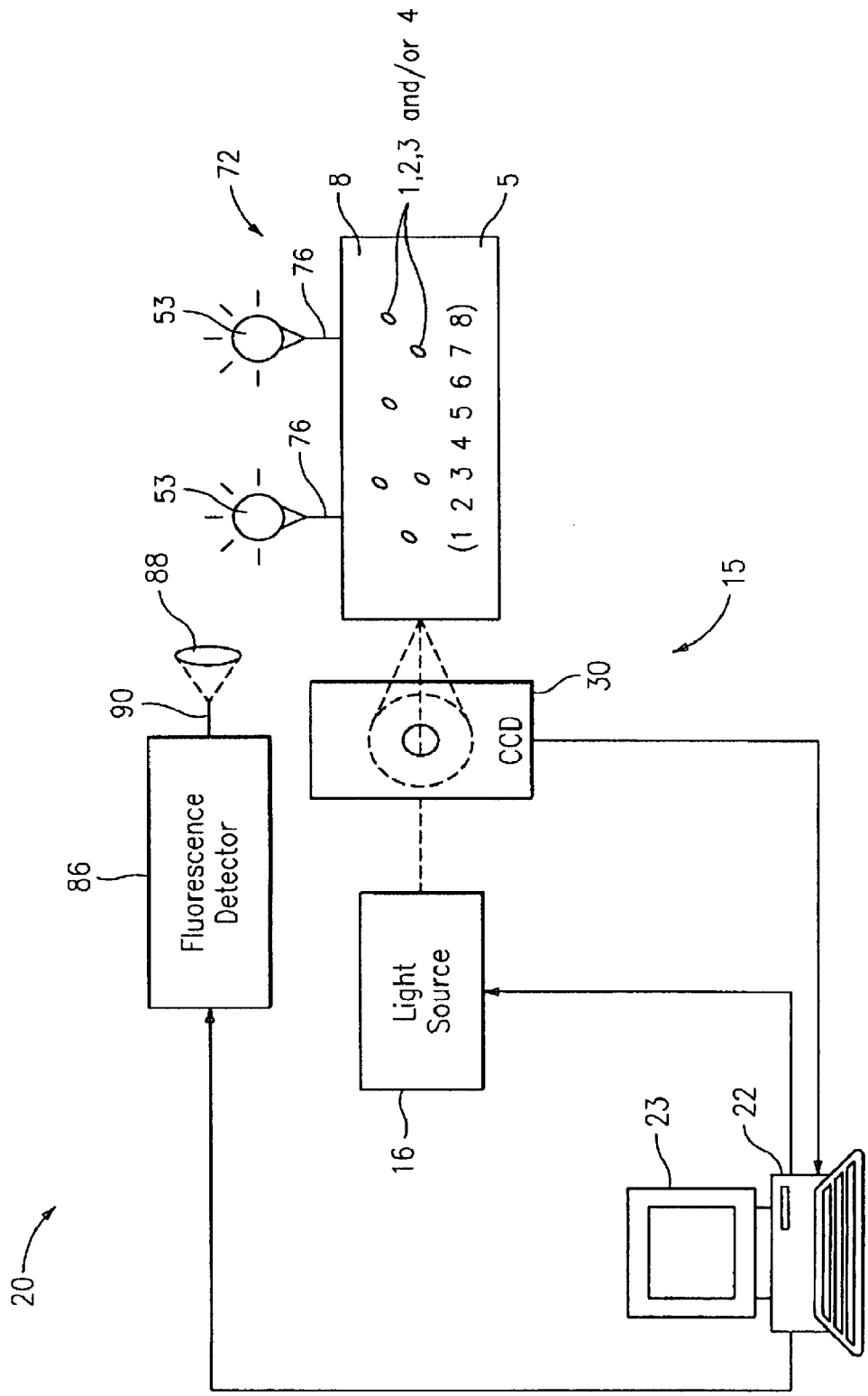
FIG. 22 is a side view of an optical identification element after the performance of an assay, and a schematic view of a bead detector that determines the code and fluorescence of the optical identification element, in accordance with various embodiments of the present invention.

As best shown in FIG. 22, each functionalized microbead 72-74 is detected for fluorescence and analyzed to determine the identification code 58 of the functionalized microbeads. A light source (not shown) may be provided to luminate the microbeads 72-74. Once the fluorescent microbeads 72-74 are identified and knowing which probe 76-78 (or single strand of DNA) was attached to each coded, functionalized microbead 72-74, the bead detector 20 determines which "target" analytes 52-54 were present in the solution 60. As described hereinbefore, the system 15 illuminates the functionalized microbeads 72-74; detects a composite X-ray diffraction pattern for each illuminated, functionalized microbead 72-74; and decodes the composite X-ray diffraction pattern to determine the code 58 of the functionalized microbead 72-74. Secondly, the bead detector 20 includes a fluorescence detector 86 for measuring the fluorescence emanating from "target" analytes 52-54 attached to the probes 76-78. The fluorescence meter 86 includes a lens 88 and optical fiber 90 for receiving and providing the fluorescence from the "target" analyte 52-54 to the fluorescence meter.

Generally, the assay of the present invention may be used to carry out any binding assay or screen involving immobilization of one of the binding agents. Such solid-phase assays or screens are well known in the chemical and biochemical arts. For example, such screening may involve specific binding of cells to a molecule (e.g. an antibody or antigen) immobilized on a microbead in the assay followed by analysis to detect whether or to what extent binding occurs. Alternatively, the beads may subsequently removed from the assay for sorting and analysis via flow cytometry (see e.g. by Needels et al. (1993). Examples of biological compounds that may be assayed or screened using the assay of the present invention include, e.g. agonists and antagonists for cell membrane receptors, toxins, venoms, viral epitopes, hormones, sugars, cofactors, peptides, enzyme substrates, drugs inclusive of opiates and steroids, proteins including antibodies, monoclonal antibodies, antisera reactive with specific antigenic determinants, nucleic acids, lectins, polysaccharides, cellular membranes and organelles. In addition, the present invention may be used in any of a large number of well-known hybridization assays where nucleic acids are immobilized on a surface of a substrate, e.g. genotyping, polymorphism detection, gene expression analysis, fingerprinting, and other methods of DNA- or RNA-based sample analysis or diagnosis.

Any of the great number of isotopic and non-isotopic labeling and detection methods well-known in the chemical and biochemical assay art may be used to detect binding with the present invention. Alternatively, spectroscopic methods well-known in the art may be used to determine directly whether a molecule is bound to a surface coating in a desired configuration. Spectroscopic methods include e.g., UV-VIS, NMR, EPR, IR, Raman, mass spectrometry and other methods well-known in the art. For example, mass spectrometry also is now widely employed for the analysis of biological macromolecules. The method typically involves immobilization of a protein on a surface of substrate where it is then exposed to a ligand binding interaction. Following ligand binding (or non-binding) the molecule is desorbed from the surface and into a spectrometer using a laser (see, e.g. Merchant and Weinberger, "Recent advancements in surface-enhanced laser desorption/ionization-time of flight-mass spectrometry," Electrophoresis 21: 1164-1177 (2000)). The microbeads in the assay of the present invention may be used as substrates in the mass spectrometry detection methods described above.

Various aspects of the present invention may be conducted in an automated or semi-automated manner, generally with the assistance of well-known data processing methods. Computer programs and other data processing methods well known in the art may be used to store information including e.g. microbead identifiers, probe sequence information, sample information, and binding signal intensities. Data processing methods well known in the art may be used to read input data covering the desired characteristics.

The invention may be used in many areas such as drug discovery, functionalized substrates, biology, proteomics, combinatorial chemistry, DNA analysis/tracking/sorting/tagging, as well as tagging of molecules, biological particles, matrix support materials, immunoassays, receptor binding assays, scintillation proximity assays, radioactive or non-radioactive proximity assays, and other assays, (including fluorescent, mass spectroscopy), high throughput drug/genome screening, and/or massively parallel assay applications. The invention provides uniquely identifiable beads with reaction supports by active coatings for reaction tracking to perform multiplexed experiments.

In particular, applications, uses, geometries and embodiments for the encoded element of the present invention may be the same as that described in the following patent applications which are all incorporated herein by reference in their entirety: U.S. patent application Ser. No. 10/661,234, filed Sep. 12, 2003, entitled "Diffraction Grating-Based Optical Identification Element"; U.S. patent application Ser. No. 10/661,031, filed Sep. 12, 2003, entitled "Diffraction Grating-Based Encoded Micro-particles for Multiplexed Experiments"; U.S. patent application Ser. No. 10/661,082, filed Sep. 12, 2003, entitled "Method and Apparatus for Labeling Using Diffraction Grating-Based Encoded Optical Identification Elements"; U.S. patent application Ser. No. 10/661,115, filed Sep. 12, 2003, entitled "Assay Stick"; U.S. patent application Ser. No. 10/661,836, filed Sep. 12, 2003, entitled "Method and Apparatus for Aligning Microbeads in order to Interrogate the Same"; U.S. patent application Ser. No. 10/661,254, filed Sep. 12, 2003, entitled "Chemical Synthesis Using Diffraction Grating-based Encoded Optical Elements"; U.S. patent application Ser. No. 10/661,116, filed Sep. 12, 2003, entitled "Method of Manufacturing of a Diffraction grating-based identification Element"; and U.S. patent application Ser. No. 10/763,995, filed Jan. 22, 2004, entitled, "Hybrid Random Bead/Chip Based Microarray", US Provisional Patent Applications, Ser. Nos. (60/609,583, 60/610,059, 60/609,712, 60/611,205, 60/610,910, 60/610,833, 60/610,829, 60/610,928, 60/611,676, and 08/915,627).

Figure 23:
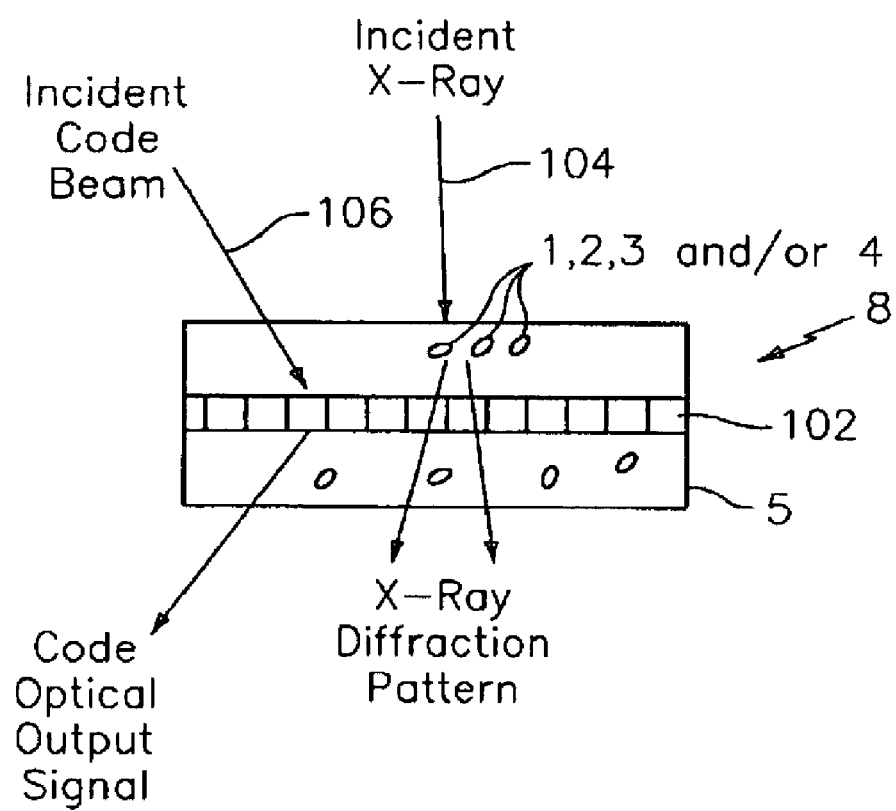
FIG. 23 is a cross-sectional view of an X-ray diffraction encoded and a diffraction grating encoded identification element in accordance with an embodiment of the present invention.

In that case, the X-ray encoding technique of the present invention would be used instead of or in addition to the diffraction based encoding described in the above patent applications. For example, as shown in FIG. 23, the substrate of binder material 5 may have at least one diffraction grating 102 each having a predetermined number of bits (as described in the aforementioned patent applications) and at least one composite X-ray diffraction pattern as described herein. The materials 1-4 provide the X-ray diffraction pattern when illuminated by an X-ray beam 104, and the incident light 106 provides the optical output signal from the diffraction grating 102. For example, the X-ray diffraction pattern may add an additional bit to the code provided by the optical output signal. Thus, the X-ray diffraction pattern adds an additional level of code multiplexing.

Some current techniques used in combinatorial chemistry or biochemistry are described in U.S. Pat. No. 6,294,327, entitled "Apparatus and Method for Detecting Samples Labeled With Material Having Strong Light Scattering Properties, Using Reflection Mode Light and Diffuse Scattering", issued Sep. 23, 2001 to Walton et al.; U.S. Pat. No. 6,242,180, entitled "Computer Aided Visualization and Analysis System for Sequence Evaluation", issued Jun. 5, 2001, to Chee; U.S. Pat. No. 6,309,823 entitled "Arrays of Nucleic Acid Probes for Analyzing Biotransformation of Genes and Methods of Using the Same", Oct. 30, 2001, to Cronin et al.; U.S. Pat. No. 6,440,667, entitled "Analysis of Target Molecules Using an Encoding System"; U.S. Pat. No. 6,355,432, entitled "Products for Detecting Nucleic Acids"; U.S. Pat. No. 6,197,506, entitled "Method of Detecting Nucleic Acids"; U.S. Pat. No. 6,309,822, entitled "Method for comparing copy number of nucleic acid sequences"; U.S. Pat. No. 5,547,839, entitled "Sequencing of surface immobilized polymers utilizing micro-fluorescence detection", U.S. Pat. No. 6,383,754, entitled "Binary Encoded Sequence Tags", and U.S. Pat. No. 6,383,754, entitled "Fixed Address Analysis of Sequence Tags", which are all incorporated herein by reference to the extent needed to understand the present invention.

The invention can be used in combinatorial chemistry, active coating and functionalized polymers, as well as immunoassays, and hybridization reactions. The invention enables millions of parallel chemical reactions, enable large-scale repeated chemical reactions, increase productivity and reduce time-to-market for drug and other material development industries.

As discussed hereinbefore, although a fluorescent label is probably most convenient, other sorts of labels, e.g., radioactive, enzyme linked, optically detectable, or spectroscopic labels may be used. An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemilumnescence would be preferred but is not required. Other detection systems may be adapted to the purpose, e.g., electron microscopy, scanning electron microscopy (SEM), scanning tunneling electron microscopy (STEM), infrared microscopy, atomic force microscopy (AFM), electrical conductance, and image plate transfer.

Unless otherwise specifically stated herein, the term "microbead" is used herein as a label and does not restrict any embodiment or application of the present invention to certain dimensions, materials and/or geometries.

The dimensions and geometries for any of the embodiments described herein are merely for illustrative purposes and, as such, any other dimensions may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. A method of labeling an item, the method comprising:
   selecting at least one material from a plurality of materials having differing X-ray diffraction patterns;
   embedding the at least one material in a binder material to form at least one optical identification element, the at least one material providing an encoded composite X-ray diffraction pattern when illuminated by an X-ray beam, the encoded composite X-ray diffraction pattern being indicative of a code, the code relating to information about the item; and
   physically associating the at least one optical identification element with the item.

2. The method of claim 1, further comprising:
   shaping the binder material as a microbead.

3. The method of claim 1, further comprising:
   shaping the binder material as a macrobead.

4. The method of claim 1, further comprising:
   shaping the binder material in the form of a thread or fiber.

5. The method of claim 1, wherein the optical identification element includes:

the binder material; and the at least one material embedded in the binder material, the at least one material being selected from powdered crystal materials.

6. The method of claim 1, wherein the code includes a binary or higher order code.

7. The method of claim 1, wherein the item comprises a nucleic acid probe.

8. The method of claim 7 wherein the nucleic acid probe is hybridized to a target nucleic acid.

9. The method of claim 1 wherein the composite diffraction pattern includes Debye-Scherrer diffraction patterns being indicative of the code.

10. The method of claim 1 wherein the code includes an error check portion configured to ensure that the code is accurate.

11. The method of claim 1 wherein the optical identification element is configured for labeling the item for at least one of sorting, tracking, identifying, verifying, and authenticating the item.

12. The method of claim 1 wherein the item comprises a chemical.

13. The method of claim 1 wherein the at least one material includes a plurality of crystal materials having predetermined Debye-Scherrer X-ray diffraction patterns.

14. The method of claim 1 wherein the item includes the binder material, said embedding the at least one material in the binder material includes embedding the at least one material directly into the item.

15. The method of claim 1 wherein the item includes material that is transparent or substantially transparent to the X-ray beam.

16. The method of claim 13 wherein the binder material does not diffract the X-ray beam or diffracts the X-ray beam in a known manner.

17. The method of claim 13 wherein the item is a chemical, said physically associating includes synthesizing the chemical on the optical identification element.

18. A method of determining information relating to an item, the method comprising:
    providing an item and an optical identification element that is physically associated with the item;
    illuminating the optical identification element using an X-ray beam;
    detecting a composite X-ray diffraction pattern from the illuminated optical identification element; and
    decoding the composite X-ray diffraction pattern to determine a code relating to information about the item.

19. The method of claim 18, wherein the decoding includes:
    identifying at least portions of Debye-Scherrer diffraction patterns in the composite X-ray diffraction pattern.

20. The method of claim 18, wherein the optical identification element is shaped as a bead.

21. The method of claim 18, wherein the code includes a binary or higher order code.

22. The method of claim 18, wherein the item comprises a nucleic acid probe.

23. The method of claim 22 wherein the nucleic acid probe is hybridized to a target nucleic acid.

24. The method of claim 18 wherein the optical identification element comprises a binder material and one or more materials embedded in the binder material, the one or more materials providing the composite X-ray diffraction pattern.

25. The method of claim 18 wherein the item comprises a probe configured to selectively bind with a target analyte, the method further comprising:
    mixing the optical identification element in a solution having the target analyte; and
    determining a presence or amount of the target analyte bound to the optical identification element.

26. The method of claim 25 wherein the determining the presence or amount of the target analyte includes detecting fluorescence emanating from the target analyte.

27. The method of claim 25 wherein the probe is directly attached to the optical identification element.

28. The method of claim 25 wherein the probe includes one of an oligonucleotide, antibody, peptide, amino acid string, cDNA, RNA, chemical, nucleic acid oligomer, polymer, biological cell, or protein.

29. The method of claim 18 wherein the optical identification element is configured for labeling the item for at least one of sorting, tracking, identifying, verifying, and authenticating the item.

30. The method of claim 18 wherein the composite diffraction pattern includes a plurality of rings projected onto a plane, said detecting includes detecting at least a portion of the rings.

31. The method of claim 30 wherein said detecting includes detecting arcs from the plurality of rings.

32. The method of claim 18 wherein the composite diffraction pattern includes diffracted beams that project forwardly in a direction of the X-ray beam and includes diffracted beams that project backwardly in a direction opposite that of the X-ray beam.

33. The method of claim 18 wherein the decoding includes identifying start and stop bits.

* * * * *